US011234743B2

United States Patent
Weiner et al.

(10) Patent No.: US 11,234,743 B2
(45) Date of Patent: *Feb. 1, 2022

(54) BONE FIXATION DEVICES AND METHODS

(71) Applicant: NEXTREMITY SOLUTIONS, INC., Warsaw, IN (US)

(72) Inventors: Lon S. Weiner, Rumson, NJ (US); Stuart D. Katchis, Scarsdale, NY (US); John R. Pepper, Cheshire, CT (US)

(73) Assignee: Nextremity Solutions, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/011,585

(22) Filed: Sep. 3, 2020

(65) Prior Publication Data
US 2021/0000517 A1     Jan. 7, 2021

Related U.S. Application Data

(63) Continuation of application No. 15/441,839, filed on Feb. 24, 2017, now Pat. No. 10,792,081, which is a continuation of application No. PCT/US2015/047377, filed on Aug. 28, 2015.

(60) Provisional application No. 62/043,237, filed on Aug. 28, 2014.

(51) Int. Cl.
*A61B 17/80*         (2006.01)

(52) U.S. Cl.
CPC ........ *A61B 17/8061* (2013.01); *A61B 17/809* (2013.01); *A61B 17/8014* (2013.01)

(58) Field of Classification Search
CPC .... A61B 17/80; A61B 17/8004; A61B 17/809
See application file for complete search history.

(56) References Cited

U.S. PATENT DOCUMENTS

| 3,741,205 A | 6/1973 | Markolf et al. |
| 3,824,995 A | 7/1974 | Getscher et al. |
| 4,009,712 A | 3/1977 | Burstein et al. |

(Continued)

FOREIGN PATENT DOCUMENTS

RU        2031635 C1     3/1995

OTHER PUBLICATIONS

International Search Report and Written Opinion of the International Searching Authority issued in PCT Application No. PCT/US2015/047377 dated Nov. 24, 2015.

(Continued)

*Primary Examiner* — Andrew Yang
(74) *Attorney, Agent, or Firm* — Heslin Rothenberg Farley & Mesiti P.C.; Victor A. Cardona, Esq.

(57) ABSTRACT

The present disclosure provides devices, systems and methods of bone fixation. The disclosed devices, systems and methods facilitate secure fixation of first and second bone segments, such as to promote fusion thereof. The devices may include at least one bone engagement projection extending from an engagement surface of a plate portion for implantation into the first bone segment. A portion of the plate portion spaced from the at least one bone engagement projection may include at least one bone fixation aperture. The least one bone fixation aperture may allow for a one bone engagement projection to be inserted therethrough and into the second bone segment to affix the plate portion to the second bone segment. In some embodiments, the at least one bone fixation aperture may be a compression slot.

14 Claims, 15 Drawing Sheets

(56) References Cited

U.S. PATENT DOCUMENTS

| | | |
|---|---|---|
| 4,565,193 A | 1/1986 | Streli |
| 4,651,724 A | 3/1987 | Berentey et al. |
| 4,960,420 A | 10/1990 | Goble et al. |
| 5,015,248 A | 5/1991 | Burstein et al. |
| 5,549,612 A | 8/1996 | Yapp et al. |
| 5,586,985 A | 12/1996 | Putnam et al. |
| 5,616,144 A | 4/1997 | Yapp et al. |
| 5,634,926 A | 6/1997 | Jobe |
| 5,662,655 A | 9/1997 | Laboureau et al. |
| 5,674,222 A | 10/1997 | Berger et al. |
| 5,785,713 A | 7/1998 | Jobe |
| 5,810,822 A | 9/1998 | Mortier |
| 6,183,475 B1 | 2/2001 | Lester et al. |
| 6,187,009 B1 | 2/2001 | Herzog et al. |
| 6,336,928 B1 | 1/2002 | Guerin et al. |
| 6,440,131 B1 | 8/2002 | Haidukewych |
| 6,656,179 B1 | 12/2003 | Schaefer et al. |
| 6,755,831 B2 | 6/2004 | Putnam et al. |
| 6,866,665 B2 | 3/2005 | Orbay |
| 7,001,388 B2 | 2/2006 | Orbay et al. |
| 7,108,697 B2 | 9/2006 | Mingozzi et al. |
| 7,341,591 B2 | 3/2008 | Grinberg |
| 7,678,113 B2 | 3/2010 | Melkent |
| 7,780,710 B2 | 8/2010 | Orbay et al. |
| 7,883,510 B2 | 2/2011 | Kim et al. |
| 8,109,980 B2 | 2/2012 | Melkent |
| 8,177,822 B2 | 5/2012 | Medoff |
| 8,470,007 B2 | 6/2013 | Melkant |
| 8,623,020 B2 | 1/2014 | Kim et al. |
| 9,101,421 B2 | 8/2015 | Blacklidge |
| 9,433,452 B2 | 9/2016 | Weiner et al. |
| 9,566,096 B2 | 2/2017 | Blacklidge |
| 9,949,773 B2 | 4/2018 | Dacosta et al. |
| 10,064,665 B2 | 9/2018 | Blacklidge |
| 2003/0153918 A1 | 8/2003 | Putnam et al. |
| 2003/0199875 A1 | 10/2003 | Mingozzi et al. |
| 2004/0127902 A1 | 7/2004 | Suzuki et al. |
| 2004/0210234 A1 | 10/2004 | Coillard-Lavirotte et al. |
| 2006/0015102 A1 | 1/2006 | Toullec et al. |
| 2006/0106387 A1 | 5/2006 | Fanger et al. |
| 2006/0241609 A1 | 10/2006 | Myerson et al. |
| 2007/0233113 A1 | 10/2007 | Kaelblein et al. |
| 2009/0118768 A1 | 5/2009 | Sixto |
| 2010/0217327 A1 | 8/2010 | Vancelette et al. |
| 2011/0208247 A1 | 8/2011 | Modi |
| 2012/0184959 A1 | 7/2012 | Price et al. |
| 2013/0046314 A1 | 2/2013 | Medoff |
| 2013/0238035 A1 | 9/2013 | Medoff |
| 2013/0267955 A1 | 10/2013 | Kubiak et al. |
| 2014/0039561 A1 | 2/2014 | Weiner et al. |
| 2015/0051650 A1 | 2/2015 | Verstreken et al. |
| 2015/0230839 A1 | 8/2015 | Riccione |
| 2016/0367298 A1 | 12/2016 | Weiner et al. |
| 2017/0164990 A1 | 6/2017 | Weiner et al. |
| 2018/0353229 A1 | 12/2018 | Blacklidge |

OTHER PUBLICATIONS

Supplemental International Search Report and Written Opinion of the International Searching Authority issued for corresponding European Patent Application No. 15835321.9 dated Sep. 13, 2018.

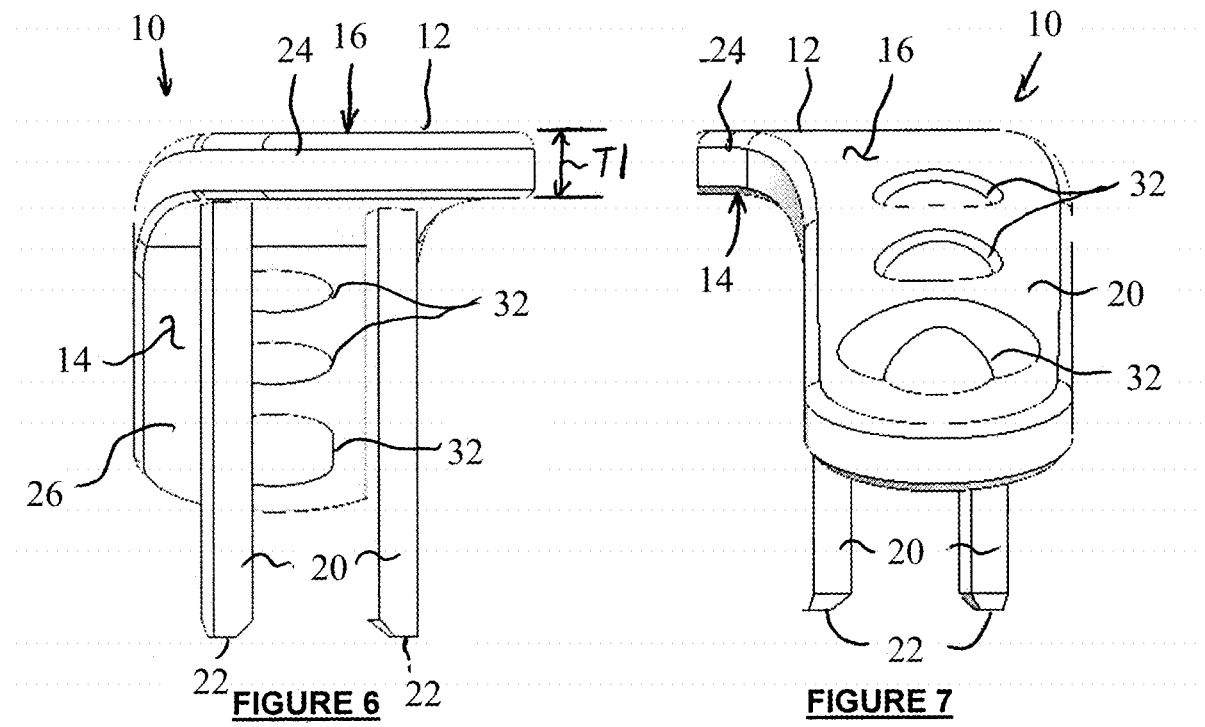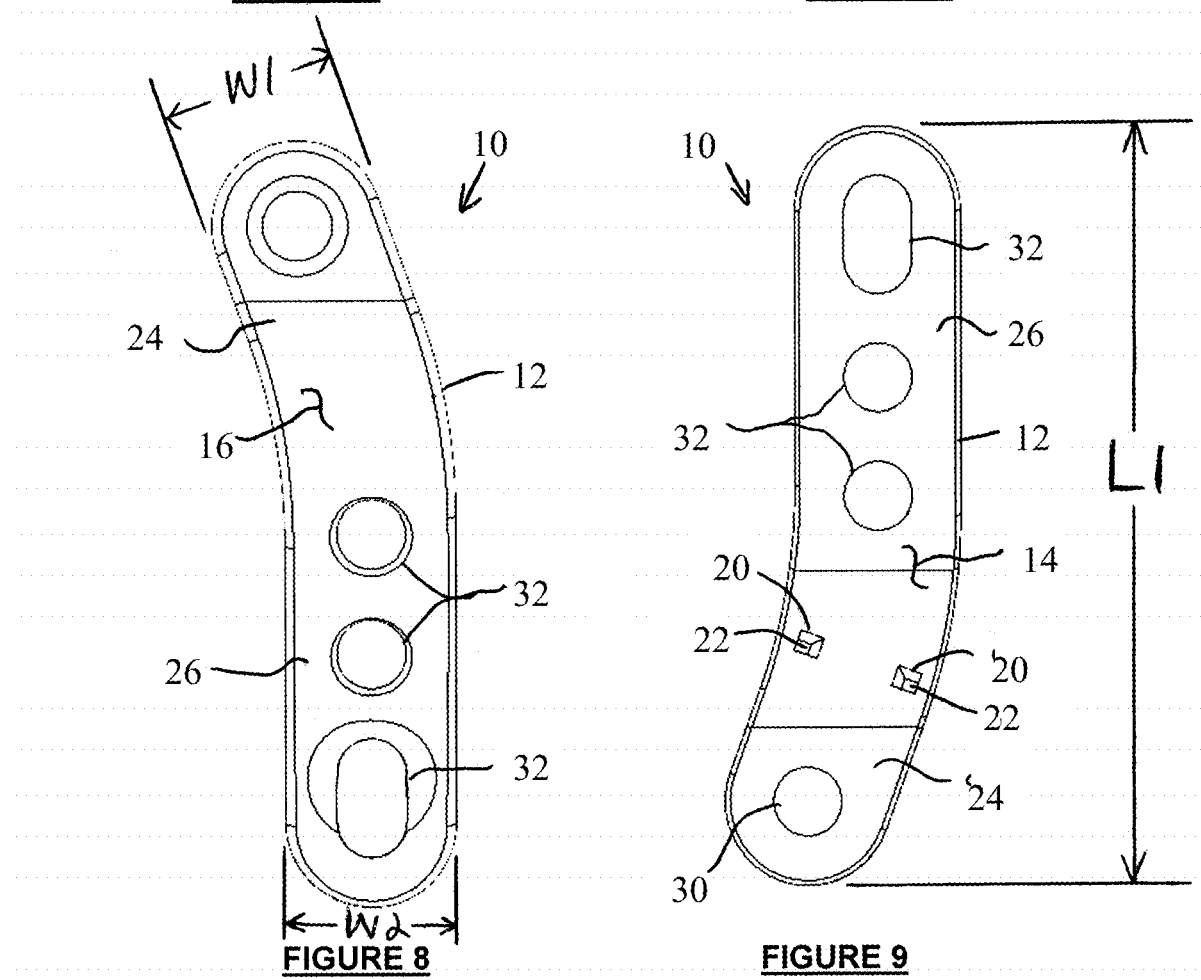

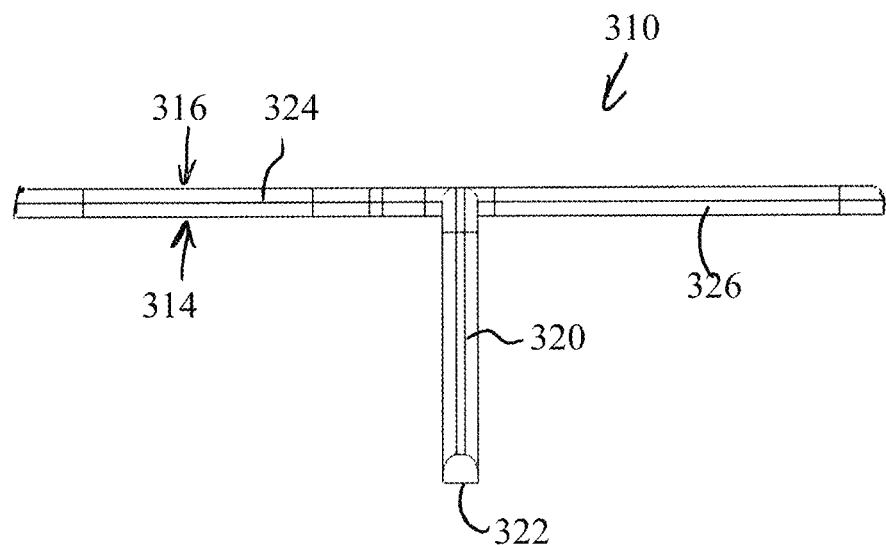
FIGURE 32
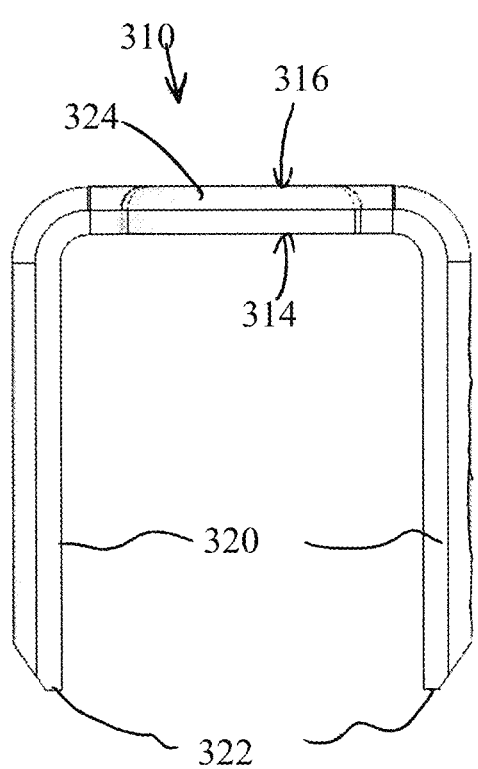 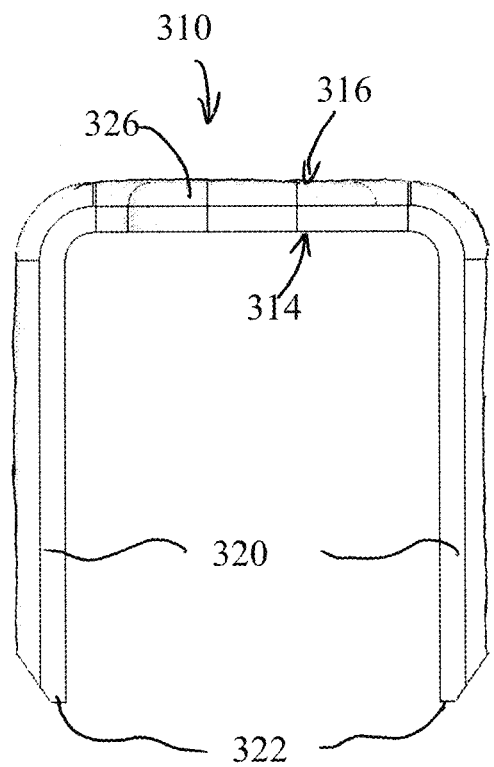
FIGURE 33 FIGURE 34

BONE FIXATION DEVICES AND METHODS

CROSS-REFERENCE TO RELATED APPLICATION

This continuation application claims priority U.S. patent application Ser. No. 15/441,839 filed Feb. 24, 2017, which is a continuation of PCT Application No. PCT/US2015/047377 filed on Aug. 28, 2015, which claimed priority to U.S. Provisional Patent Application No. 62/043,237, which was filed on Aug. 28, 2014, and entitled Bone Fixation Device and Method, the entireties of which are hereby expressly incorporated herein by reference.

TECHNICAL FIELD

The present disclosure relates to bone fixation and/or fusion devices, systems and methods.

BACKGROUND OF THE INVENTION

An ideal fusion is one having solid and sustained bone contact at the conclusion of a surgical procedure and also keeping sustained bone contact for the weeks following the surgical procedure for the bone remodeling process to unite the bones. Failure to maintain proper fixation to keep sustained bone contact can result in misalignment, malunion, nonunion, and ongoing pain for the patient.

A single screw or pin utilized with current bone plates is typically not enough to eliminate all degrees of freedom of motion between bones for fixation. As a result, plating of even relatively small bones typically requires numerous screws or pins to capture the bones, which is impractical, as this may fracture or at least weaken the bones. As opposed to bone plates with numerous screws or pins, staples are low profile, but have limited compression ability.

Accordingly, alternative devices, systems and methods of bone fixation and/or fusion are desired.

SUMMARY

In one aspect, the present disclosure provides for a fixation device for fixing bone segments. The fixation device plate portion and at least a pair of bone engagement projections extending from the plate portion for implantation into the first bone segment. The plate portion includes a proximal portion with at least one fixation aperture configured for acceptance of a bone fixation mechanism therethrough and into a first bone segment. The plate portion also includes a distal portion with a plurality of bone fixation apertures configured for acceptance of a bone fixation mechanism therethrough and into a second bone segment.

In some embodiments, the proximal and distal portions each include a substantially planar portion. In some embodiments, the proximal and distal portions are angled with respect to each other in the medial-lateral direction. In some embodiments, the proximal and distal portions are angled with respect to each other in the plantar-dorsal direction. In some such embodiments, the bone engagement projections extend from the plate portion in the plantar-dorsal direction, and the distal portion extends further in the plantar-dorsal direction than the bone engagement projections when the proximal portion is orientated substantially horizontally. In some other such embodiments, the bone engagement projections extend from the plate portion in the plantar-dorsal direction a distance further than that of the distal portion when the proximal portion is orientated substantially horizontally.

In some embodiments, the proximal and distal portions are elongated in the proximal-distal direction, and the distal portion defines a total length in the proximal-distal direction greater than a total length of the proximal portion in the proximal-distal direction. In some embodiments, the proximal and distal portions each define a width in the medial-lateral direction, and the width of the proximal portion is greater than the width of the distal portion. In some such embodiments, the distal portion is elongated in the proximal-distal direction, and the width of the distal portion tapers as it extends in the proximal-distal direction away from the proximal portion. In some such embodiments, the distal portion includes a narrow region in the medial-lateral direction positioned at least partially between a pair of bone fixation apertures in the proximal-distal direction.

In some embodiments, the bone engagement projections extend from a bone engagement surface of the proximal portion. In some such embodiments, the bone engagement projections extend normally from the engagement surface of the proximal portion. In some embodiments, the bone engagement projections extend the distal portion as they extend from the plate portion. In some embodiments, the bone engagement projections extend from a medial-lateral side of the plate portion. In some embodiments, at least one of the plurality of bone fixation apertures of the distal portion is a compression slot.

In another aspect, the present disclosure provides for a fixation device for fixing bone segments. The fixation device includes a plate portion and at least a pair of bone engagement projections. The plate portion includes at least one fixation aperture configured for acceptance of a bone fixation mechanism therethrough and into a first bone segment. The plate portion also includes a distal portion including a plurality of bone fixation apertures configured for acceptance of a bone fixation mechanism therethrough and into a second bone segment. The at least a pair of bone engagement projections extend from the plate portion for implantation into the first bone segment to substantially fix the first and second segments with respect to each other. The proximal and distal portions are elongated and angled with respect to each other in the medial-lateral direction and the plantar-dorsal direction.

In some embodiments, the plate portion includes a bone engagement surface defined by the proximal and distal portions, and the engagement surface of the plate portion is concave. In some embodiments, the proximal and distal portions are angled with respect to each other in the medial-lateral direction equal to or less than about 60 degrees and with respect to each other in the plantar-dorsal direction equal to or less than about 60 degrees. In some embodiments, the distal portion includes at least two bone fixation apertures. In some such embodiments, at least one of the at least two bone fixation apertures of the distal portion is a compression slot.

In some embodiments, proximal and distal portions are elongated in the proximal-distal direction, and the distal portion defines a total length that is greater than a total length defined by the proximal portion. In some embodiments, the bone engagement projections extend from the plate portion in the plantar-dorsal direction, and the distal portion extends further in the plantar-dorsal direction than the bone engagement projections when the proximal portion is orientated substantially horizontally. In some embodiments, the bone engagement projections extend from the plate portion in the plantar-dorsal direction a distance further than that of the distal portion when the proximal portion is orientated substantially horizontally. In some embodiments, the bone engagement projections define a plane, and the plane extends substantially perpendicular to the proximal portion.

In some embodiments, the proximal and distal portions of the plate portion are substantially planar. In some such embodiments, the plate portion includes an arcuate intermediate portion extending between the proximal and distal portions, and the bone engagement projections extend from the intermediate portion. In some such embodiments, the intermediate portion is arcuate in the medial-lateral and plantar-dorsal directions to bi-angle the proximal and distal portions with respect to each other.

In another aspect, the present disclosure provides for a fixation device for fixing bone segments including a substantially planar plate portion and at least a pair of bone engagement projections. The plate includes a proximal portion defining a first width in the medial-lateral direction and including at least a pair of fixation apertures configured for acceptance of a bone fixation mechanism therethrough and to engage a first bone segment. The plate portion further includes a distal portion defining a second width in the medial-lateral direction that is less than the first width and including a compression slot configured for acceptance of a bone fixation mechanism therethrough and to engage a second bone segment. The at least a pair of bone engagement projections extend from the proximal portion of the plate portion for implantation into the first bone segment to substantially fix the first and second bone segments to each other.

In some embodiments, the distal portion is elongated in the proximal-distal direction, and the width of the distal portion tapers as it extends in the proximal-distal direction away from the proximal portion. In some such embodiments, the distal portion includes a fixation aperture spaced from the compression slot in the proximal-distal direction toward the proximal portion. In some such embodiments, the distal portion includes a narrow region in the medial-lateral direction positioned at least partially between the compression slot and bone fixation aperture in the proximal-distal direction.

In some embodiments, at least one bone engagement projection is proximate to each of the fixation apertures of the proximal portion and positioned proximate to an end of the proximal portion in the proximal-distal direction. In some embodiments, the pair of bone engagement projections extend in the proximal-distal direction toward the distal portion. In some embodiments, the pair of fixation apertures are positioned proximate to opposing ends of the proximal portion in the medial-lateral direction.

In another aspect, the present disclosure provides for a fixation device for fixing bone segments. The fixation device includes a substantially planar plate portion and at least a pair of bone engagement projections. The plate portion includes a proximal portion having a second end and including at least one fixation aperture configured for acceptance of a bone fixation mechanism therethrough and into a first bone segment. The plate portion also includes distal portion having a second end and including a compression slot configured for acceptance of a bone fixation mechanism therethrough and into a second bone segment. The at least a pair of bone engagement projections extend from opposing medial-lateral sides of an intermediate portion of the plate portion for implantation into the first bone segment to substantially secure the first and second segments together.

In some embodiments, the plate portion is deformable into a non-planar shape. In some embodiments, the proximal and distal portions are elongated along the proximal-distal direction. In some such embodiments, the proximal and distal portions extend substantially linearly along a central axis extending through the first and second ends. In some embodiments, the distal portion further includes a fixation aperture configured for acceptance of a bone fixation mechanism therethrough. In some such embodiments, the compression slot and the fixation aperture of the distal portion are spaced along the direction of a central axis extending through the first and second ends, and the fixation aperture of the distal portion is positioned proximate to the second end.

In some embodiments, the at least a pair of bone engagement projections extend in the medial-lateral direction as they extend from the opposing medial-lateral sides of the intermediate portion of the plate portion and extend in the plantar-dorsal direction therefrom. In some embodiments, the proximal and distal portions each define a width in the medial-lateral direction, and the width of the distal portion is greater than the width of the proximal portion. In some such embodiments, the proximal portion includes a portion that defines a width in the medial-lateral direction that is equal to a width of the distal portion in the medial-lateral direction.

These and other objects, features and advantages of this disclosure will become apparent from the following detailed description of the various aspects of the disclosure taken in conjunction with the accompanying drawings.

BRIEF DESCRIPTION OF THE DRAWINGS

FIG. 6 is front view of the fixation device of FIG. 2;

FIG. 7 is a back view of the fixation device of FIG. 2;

FIG. 8 is top view of the fixation device of FIG. 2;

FIG. 9 is a bottom view of the fixation device of FIG. 2;

FIG. 32 is a right-side view of the fixation device of FIG. 29;

FIG. 33 is a back view of the fixation device of FIG. 29;

FIG. 34 is a front view of the fixation device of FIG. 29;

DETAILED DESCRIPTION

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Figure 1:
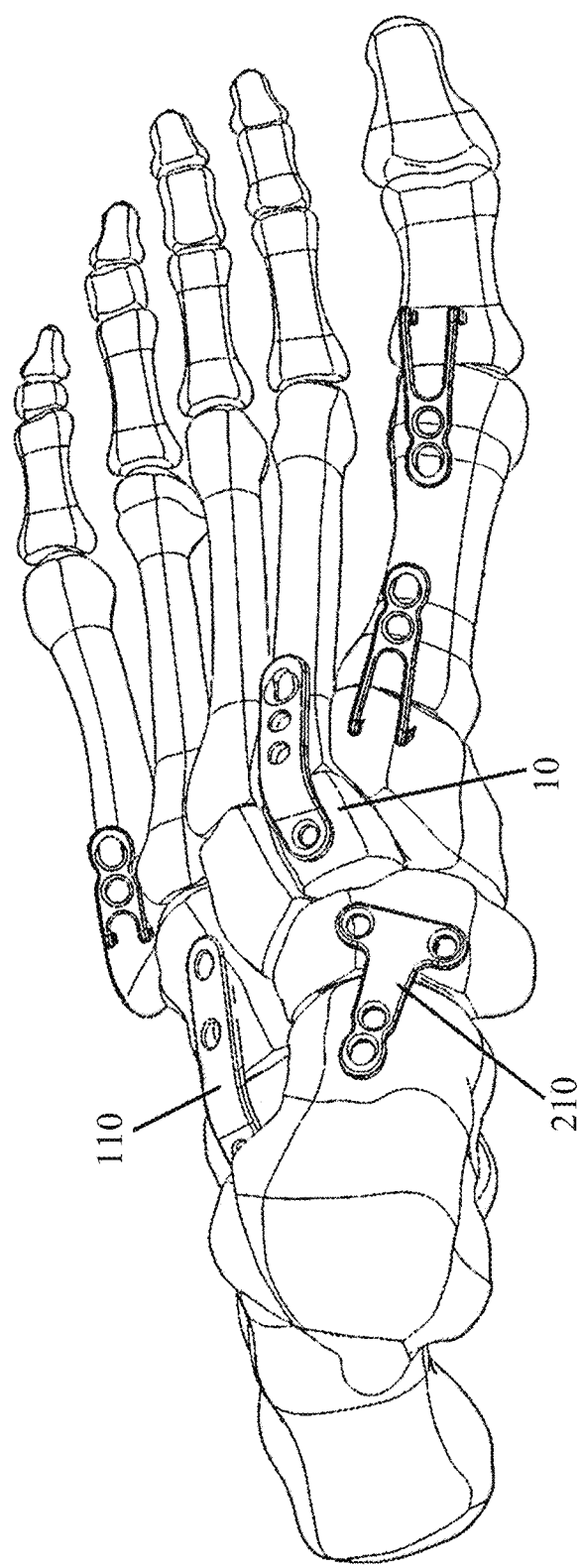
FIG. 1 is a top view of exemplary fixation devices of the present disclosure implemented with bone segments of a foot.

The present disclosure provides devices, systems and methods of bone fixation. The disclosed devices, systems and methods facilitate secure fixation of first and second bone segments as shown in FIG. 1. As shown in FIG. 1, the devices, systems and methods of the present disclosure may include a plate portion that is coupled to a first bone segment and a second bone segment to configure or place the bone segments into a corrective construct. The term "bone segment" or simply "segment" is used herein to refer to a portion of a bone or boney tissue. A bone portion may be a distinct bone structure or may be a section of a larger bone structure. For example, a first bone segment may be a portion of a first bone and a second bone segment may be another portion of the first bone, and the first and second portions may be delineated (at least in part) by a fracture, cut, joint or other discontinuity. As another example, a first bone segment may be a first bone and a second bone segment may be second bone that is a separate and distinct from the first bone.

In the various embodiments described herein and corresponding with the Figures provided herewith, bone fixation devices, methods and system are described with bone segments of the foot. However, other bones segments may be utilized with the devices, system and methods of the current disclosure, such as other relatively small bones. For example, bones of the hand, wrist, ankle, spine, cranium, etc. may be utilized with the devices, system and methods of the current disclosure. As shown in FIG. 1 and described further below, some embodiments of the devices, system and methods of the current disclosure may be particularly advantageous for fixation and/or fusion of bone segments of the foot. For example, as shown in FIG. 1 the present disclosure provides devices or systems 10 (and related methods) that are particularly advantageous for fixation and/or fusion of bone segments of a Talar Navicular joint. As another example also shown in FIG. 1, the present disclosure provides devices or systems 110 (and related methods) that are particularly advantageous for fixation and/or fusion of bone segments of a Lis Franc joint. As a further example shown in FIG. 1, the present disclosure provides devices or systems 210 (and related methods) that are particularly advantageous for fixation and/or fusion of bone segments of a Calcaneal cuboid joint. As yet another example shown in FIG. 1, the present disclosure provides devices or systems (and related methods) that are particularly advantageous for fixation and/or fusion of the first metatarsal and an adjacent bone segment.

Before implementation of the bone devices, systems and methods described herein, both a first bone segment and a second bone segment may be cut. In alternative embodiments, at least one of the first and second bone segments may not be cut. In some embodiments, the first and second bone segments may be formed, at least in part, due to a fracture, and the devices, systems and methods may be utilized for fracture fixation to facilitate fusion of the fractured segments (i.e., correction of the fracture). In some embodiments, a plate portion of the devices may be positioned over a first bone segment and a second bone segment such that a proximal portion of the plate portion including at least one bone engagement projection extending therefrom, such as at least one claw or tine, is positioned over the second bone segment and a distal portion of the plate portion including a fixation aperture for receiving a bone fixation member therethrough is positioned over the first bone segment. The at least one bone engagement projection can be inserted into the second bone segment to couple or attach the plate portion to the first bone segment. A bone fixation mechanism or member may be inserted (e.g., screwed) through the fixation aperture of the plate portion and into the first bone segment to couple or attach the first bone segment to the plate portion. In some embodiments, the fixation aperture may be a compression slot and the bone fixation member may be a screw such that tightening of the screw causes the plate portion to translate with respect to the first bone segment such that the at least one engagement projection causes the second bone segment to move toward and at least abut the first bone segment to form a corrective construct. Alternatively, in place of a compression slot, a substantially circular aperture and/or a non-compressive slot may be included for securing the first and bone segments in a fixed position or angle via a bone fixation member extending therethrough.

Figure 10:
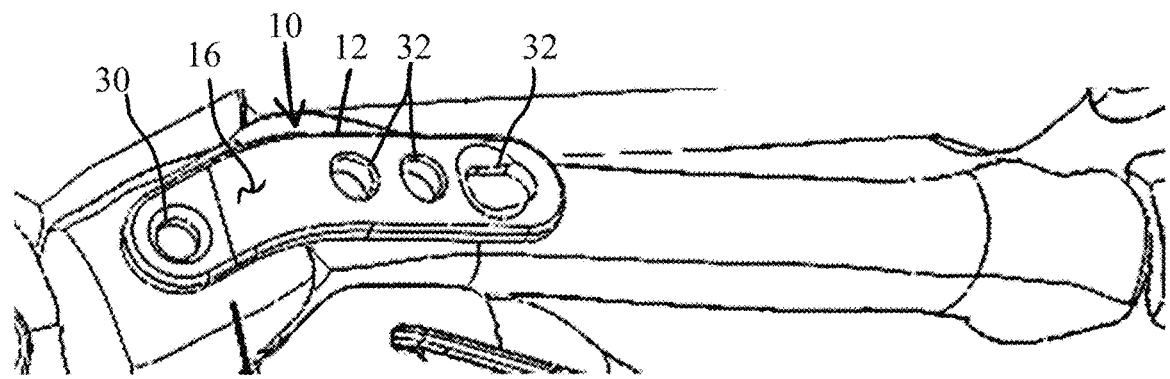
FIG. 10 an elevational perspective view of the fixation device of FIG. 2 implemented with bone segments of an exemplary the Lis Franc joint.
Figure 11:
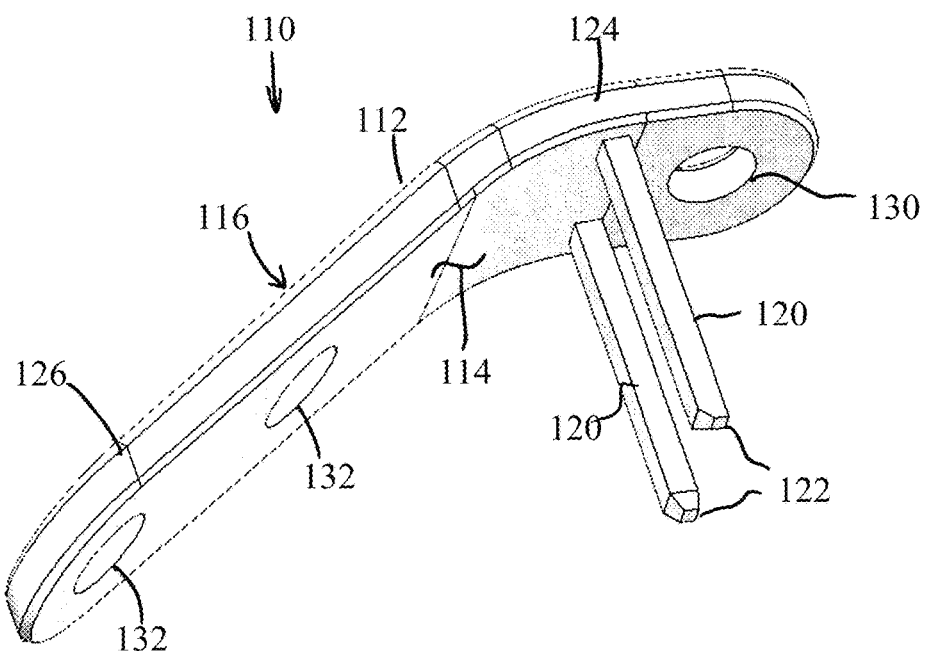
FIG. 11 is a bottom perspective view of the Calcaneal-Cuboid joint fixation device of FIG. 1 according to the present disclosure.
Figure 12:
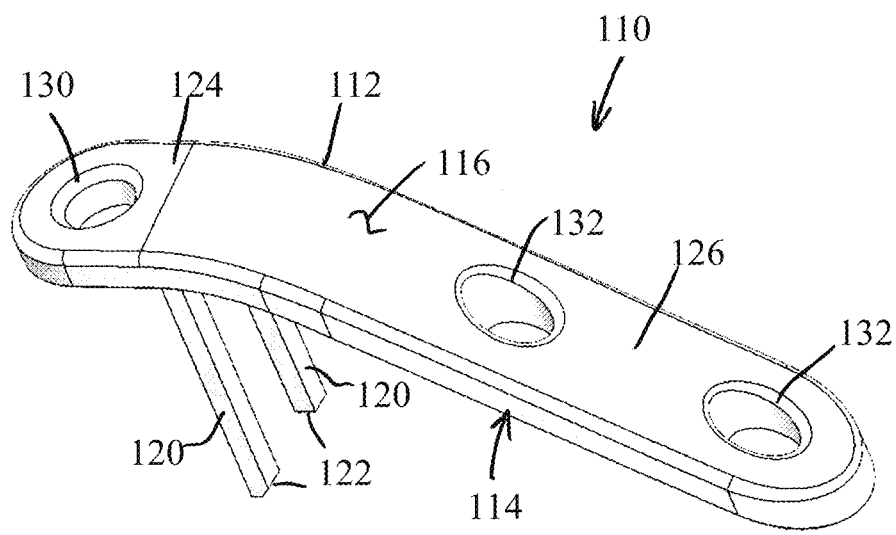
FIG. 12 is an elevational perspective view of the fixation device of FIG. 11.

An example of a fixation device 10 that promotes or achieves bone fusion according to the present disclosure is shown in FIGS. 2-10. The device 10 of FIGS. 2-10 may be particularly well suited for fixation of the bone segments of the Lis Franc joint, as shown in FIGS. 1 and 10. As shown in FIGS. 1-7, the device 10 may include at least one bone engagement projection 20 extending from an engagement surface 14 of a plate portion 12 (e.g., an inferior-facing surface of the plate portion). In one example, the device 10 includes a pair of bone engagement projections 20, 20 extending from the engagement surface 14 of the plate portion 12, as shown in FIGS. 2-7 and 9. The at least one bone engagement projection 20 defines a free end 22 that is configured to penetrate into a bone segment, as shown in FIGS. 2-7 and 9.

The at least one bone engagement projection 20 may extend from a proximal portion 24 of the plate portion 12, or at about a junction or transition portion between the proximal portion 24 and a distal portion 26 of the plate portion 12, as shown in FIGS. 2-7 and 9. In alternative embodiments, the distal portion 26 of the plate portion 12 may include the at least one bone engagement projection 20. The at least one bone engagement projection 20 may extend from a bone engagement surface or side 14 of the plate portion 12 that is configured to abut or overlie bone or other tissue, such as the first and second bone segments. Each of the at least one engagement projections 20 may be configured to engage and attach within a second bone segment. The at least one bone engagement projection 20 may include teeth, barbs, surface texture or any other surface irregularity for biting into or otherwise securing with the second bone segment to support improved fixation of the device 10 to the second bone segment (and, potentially, the first bone segment). The at least one bone engagement projection 20 may alternatively be tines, staples or claw members. Additionally, the at least one bone engagement projection 20 may include a plurality of notches, grooves, ramps, plateaus, pitting or a non-uniform surface, texture and/or coating to facilitate attachment to the second bone segment and, potentially, compression between the first and second bone segments.

Figure 2:
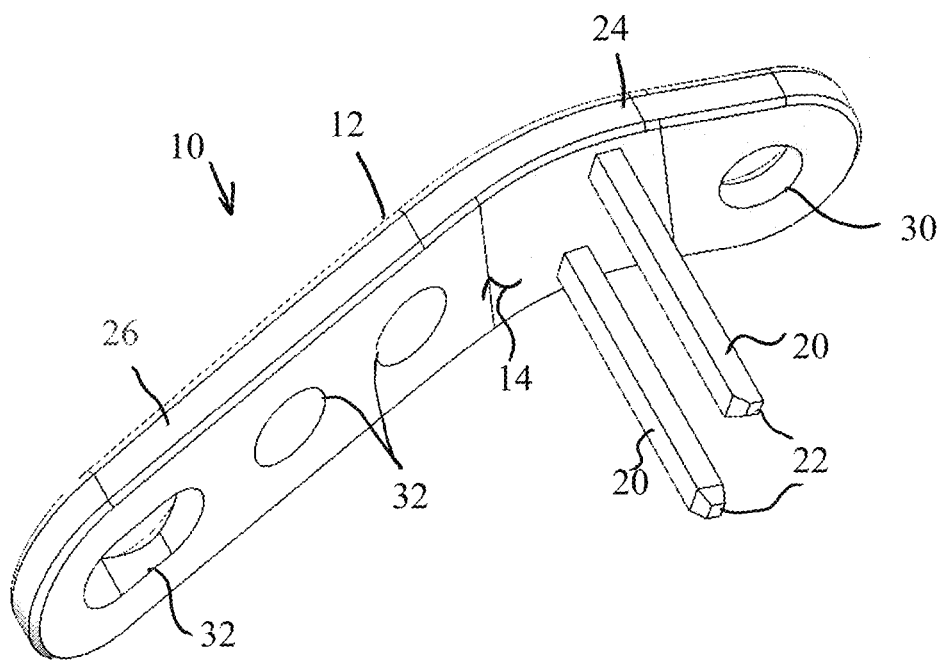
FIG. 2 is a bottom perspective view of the Lis Franc joint fixation device of FIG. 1 according to the present disclosure.
Figure 3:
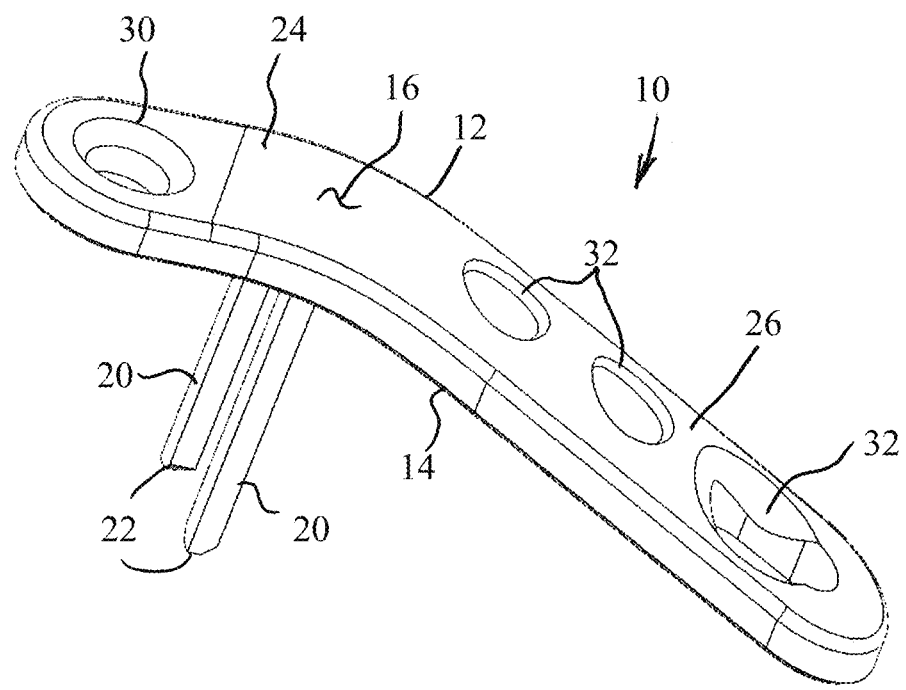
FIG. 3 is an elevational perspective view of the fixation device of FIG. 2.
Figure 4:
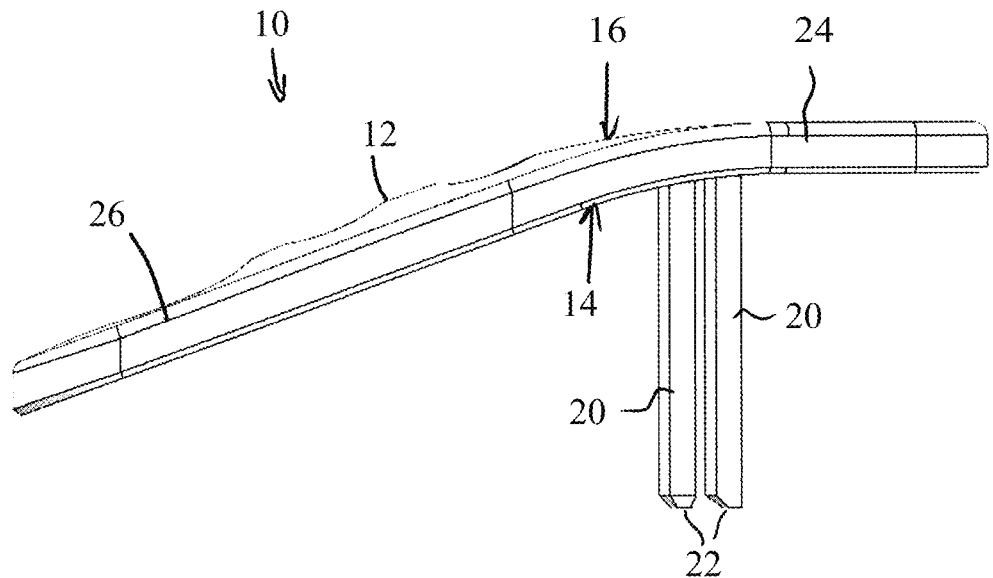
FIG. 4 is left side view of the fixation device of FIG. 2.
Figure 5:
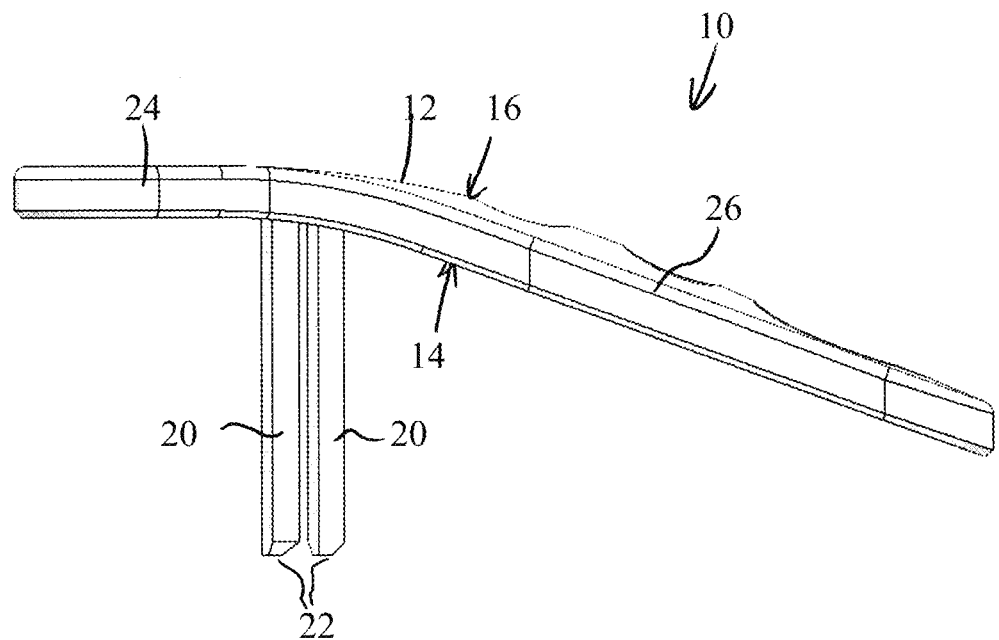
FIG. 5 is a right side view of the fixation device of FIG. 2.

The at least one bone engagement projection 20 may be positioned or oriented at an angle or an offset from another portion of the device 10, such as from the distal portion 26 26 of the plate portion 12, as shown in FIGS. 2-7 and 9. For example, as shown in FIGS. 4 and 5, the at least one bone engagement projection 20 may extend substantially perpendicular or normal from the proximal portion 24 of the plate portion 12 but angled with respect the distal portion 26 of the plate portion 12. The at least one bone engagement projection 20 may be orientated at an acute angle to the distal portion 26 of the plate portion 12 such that the at least one bone engagement projection 20 is angled in the proximal-to-distal direction as they extend from the engagement surface 14 in the dorsal-to-plantar direction.

In some embodiments, the at least one bone engagement projection 20 may be round, rectangular or polygonal in cross-section (e.g., in the transverse plane). In other embodiments, the at least one bone engagement projection 20 or members may include other cross-sectional shapes. The at least one bone engagement projection 20 may define a cross-sectional width within the range of about ½ mm to about 5 mm. The at least one bone engagement projection 20 may define a total length from the engagement surface of the plate portion 12 to the free ends thereof within the range of about 5 mm to about 30 mm.

As noted above, the at least one bone engagement projection 20 may be configured to extend into and engage a second bone segment (and/or abut against a side of a bone segment, such as being positioned within a joint space). The at least one bone engagement projection 20 may be effective at stabilizing a second bone segment that is too small or oddly proportioned to be engage with multiple bone fixation mechanisms (e.g., screws or pins). The fixation afforded by the at least one bone engagement projection 20 (e.g., a pair of bone engagement projections 20, 20) may be necessary to stabilize particular first bone segments. In some embodiments, an aperture or hole corresponding to each at least one bone engagement projection 20 may be formed (e.g., via drilling) in the second bone segment. The formation of holes or apertures within the second bone segment may be formed with the use of a guide to form the holes at distances, orientations, etc. that correspond with each of the at least one bone engagement projection 20. After formation of such apertures, the at least one bone engagement projection 20 may then be inserted into the corresponding aperture(s). In other embodiments, the at least one bone engagement projection 20 may be inserted into the second bone segment, such a downward stapling force, from any device capable of applying such force to insert the at least one bone engagement projection 20 into the second bone segment.

In some embodiments, the proximal portion 24 of the plate portion 12 may include at least one fixation aperture 30 in addition to the at least one at least one bone engagement projection 20, as shown in FIGS. 2, 3 and 7-10. The at least one fixation aperture 30 of the proximal portion 24 of the plate portion 12 may be positioned further in the proximal direction than the at least one bone engagement projection 20, as shown in FIGS. 2, 3 and 9. The at least one fixation aperture 30 of the proximal portion 24 may be configured to accept a bone fixation member therethrough (not shown), such as a bone screw, nail or pin. The at least one fixation aperture 30 of the proximal portion 24 of the plate portion 12 and a corresponding at least one bone fixation member (not shown) may be effective, in combination with the at least one at least one bone engagement projection 20, to provide multiple points of contact with the second bone segment to securely hold or engage the second bone segment and promote fusion with the first bone segment (as described further below). The at least one fixation aperture 30 of the proximal portion 24 of the plate portion 12, and the corresponding at least one bone fixation member, may define a cross-sectional width or diameter within the range of about 2 mm to about 6 mm. As shown in FIGS. 3, 7 and 8, the at least one fixation aperture 30 of the proximal portion 24 of the plate portion 12 may include a countersink at the top surface 16 of the plate portion 12 to seat the top edge of the corresponding at least one bone fixation member even with or below the top surface 16 of the plate portion 12.

While bone screws, nails or pins may be mentioned herein as potential bone fixation mechanisms or members, any fixation member may be used in place of a bone screw, nail or pin. A bone fixation member utilized with the devices provided herein may be any elongated fixation mechanism or member, such as but not limited to a screw, pin, bolt, nail, wire or the like. The bone fixation mechanisms of the present disclosure interact with the fixation apertures in the plate to cause engagement of the particular portion of the plate portion with a corresponding bone segment positioned there below. The bone fixation mechanisms may also include fixation structures such as barbs or surface irregularities thereon to promote attachment to the bone segments.

As shown in FIGS. 2-10, the distal portion 26 of the plate portion 12 may also include at least one bone fixation aperture 32 configured to accept a bone fixation mechanism or member, such as bone screw, nail or pin, therethrough. For example, the distal portion 26 of the plate may include two substantially circular apertures 32, 32 and an extend aperture or slot (e.g., a compression slot) 32 spaced in the proximal-distal direction, with the slot 32 being positioned distal to the two circular apertures 32, 32. An aperture or pilot hole may be formed in the first bone segment corresponding to each bone fixation aperture 32 of the distal portion 26 of the plate portion 12 to facilitate insertion of a corresponding bone fixation mechanism through each aperture and into the first bone segment. The at least one bone fixation aperture 32 of the distal portion 26 of the plate portion 12 and corresponding bone fixation member(s) are utilized to affix the first bone segment to the distal portion 26 of the plate portion 12. In this way, as shown in FIG. 10, the plate portion 12 spans a joint, fracture or other discontinuity extending at least partially between the first and second bone segments, with the proximal portion 24 of the plate portion 12 affixed to the second bone segment via the at least one bone engagement projection 20 and at least one fixation mechanism (e.g., a screw), and the distal portion 26 of the plate portion 12 affixed to the first bone segment via the at least one bone fixation mechanism (e.g., a screw).

The inclusion of a compression slot 32 in the distal portion 26 of the plate portion 12 may be effective in reducing or compressing the junction of the first and second bone segments, as shown in FIGS. 2-10. For example, a bone screw or the like may be screwed into first bone segment through the compression slot 32 in the distal portion 26 of the plate portion 12 after a pilot hole has been drilled into the first bone segment. The compression slot 32 may be shaped such that as the bone screw is screwed into first bone segment through a first portion of the compression slot 32, the compression slot 32 effectuates movement of the screw into a second portion of the compression slot 32 (i.e., movement of the plate portion 12 with respect to the screw) such that the second bone segment and first bone segment are forced to move towards each other to form a corrective bone construct. For example, the compression slot 32 may include an angled, curved profiled surface proximate to a through hole, and a head or expanded portion of a bone fixation member may contact the profiled surface as it is inserted into a bone segment and to translate the bone fixation member and the device 10 with respect to each other. In some embodiments, the compression slot 32 in the distal portion 26 of the plate portion 12 may be the outermost bone fixation aperture 32 of the distal portion 26 (i.e., the most-distal bone fixation aperture 32).

As shown in FIG. 8, the medial-lateral widths W1, W2 of the proximal and distal portions 24, 26 of the plate portion 12 may be substantially equal. In some alternative embodiments, the medial-lateral width W1, W2 of the proximal and distal portions 24, 26 of the plate portion 12 may differ. The total medial-lateral width W1, W2 of the proximal and/or distal portions 24, 26 of the plate portion 12 of the device 10 may be within the range of about 4 mm to about 20 mm. As shown in FIG. 9, the total length L1 of the plate portion 12 of the device 10 in the proximal-distal direction may be within the range of about 10 mm to about 250 mm. As shown in FIG. 6, the total thickness T1 of the plate portion 12 of the device 10 in the plantar-dorsal direction may be within the range of about 1 mm to about 6 mm.

The plantar-dorsal thickness T1 of the plate portion 12 may vary such that the plate portion 12 is shaped and contoured to substantially match the arrangement and shape of the first and second bone segments. For example, the proximal and distal portions 24, 26 of the plate portion 12 extending about the apertures 30, 32 and the at least one bone engagement projection 20 may have a first thickness or may include or be formed of a first material, and the portion of the plate portion 12 therebetween may have a second thickness or include or be formed of a second material. The first thickness may be greater than the second thickness or less than the second thickness. The first material may be more rigid or stiff than the second material and the second material may be more flexible or malleable than the first material. Thus, any portion of the plate portion 12 may be composed of different materials, different thicknesses, different stiffness or other different mechanical properties or characteristics. In some embodiments, the plate portion 12 may be made of a biocompatible material, such as metal or alloy (e.g., stainless steel, nitinol, and titanium). In some embodiments, the plate portion 12 may be made of a bioabsorbable, composite and/or polymer material.

As noted above, the device 10 of FIGS. 2-10 may be configured such that it is particularly advantageous for use with a Lis Franc joint, with the proximal portion 24 of the plate portion 12 fixed to one of the tarsal bones (i.e., the second bone segment) and the distal portion 26 of the plate portion 12 fixed to a corresponding metatarsal bone (i.e., the first bone segment). In such an embodiment, the proximal and distal portions 24, 26 of the plate portion 12 may not be aligned or extend straight in the proximal-distal direction. As shown in FIGS. 2-10, the proximal and distal portions 24, 26 of the plate may be offset or angled with respect to each other in the medial-lateral direction. As shown in FIGS. 8 and 9, the distal portion 26 of the plate portion 12 may be offset or angled with respect to the proximal portion 24 of the plate portion 12 in the medial-lateral direction. The distal portion 26 may be offset or angled with respect to the proximal portion 24 of the plate portion 12 in the medial-lateral direction within about 5 degrees to about 60 degrees. The intersection region or point between the proximal and distal portions 24, 26 of the plate portion 12 in the medial-lateral direction may be arcuate or curved, and the proximal and distal portions 24, 26 may extend substantially linearly.

As shown in the plantar-to-dorsal view of FIG. 9, the device 10 may include a pair of bone engagement projections 20, 20 that are arranged such that a plane intersecting the projections 20, 20 is angled or offset from the proximal portion 24 of the plate portion 12. For example, as shown in FIG. 9 the pair of bone engagement projections 20, 20 may be are arranged such that a plane intersecting the projections 20 is perpendicular to the direction that the proximal portion 24 is extended. In this way, the pair of bone engagement projections 20, 20 may likewise be offset or angled with respect to the distal portion 26 of the plate portion 12 (e.g., a plane intersecting the projections 20 may be angled 90 degrees plus or minus about 5 degrees to about 60 degrees from the distal portion 26 in the medial-lateral direction, depending upon the medial-lateral side the measurement is taken).

As also shown in FIGS. 2-10, the distal portion 26 of the plate portion 12 may define a longer total proximal-distal length as compared to that of the proximal portion 24 of the plate portion 12. For example, the distal portion 26 of the plate portion 12 may form about ⅔ of the total proximal-distal length of the entirety of the plate portion 12 (and, therefore, the proximal portion 24 of the plate portion 12 may form about ⅓ of the total proximal-distal length of the entirety of the plate portion 12). Still further, as shown in FIGS. 5 and 6, the proximal and distal portions 24, 26 of the plate portion 12 may not be aligned in the plantar-dorsal direction. For example, the proximal and distal portions 24, 26 of the plate portion 12 may be planar, but offset or angled with respect to each other in the plantar-dorsal direction. Specifically, the proximal and distal portions 24, 26 of the plate portion 12 may be offset or angled with respect to each other within about 5 degrees to about 60 degrees in the plantar-dorsal direction. As shown in FIGS. 4 and 5, the bone engagement projections may extend further in the plantar-dorsal direction than the distal portion 26 of the plate portion 12 when the proximal portion 24 is oriented substantially horizontally.

Figure 17:
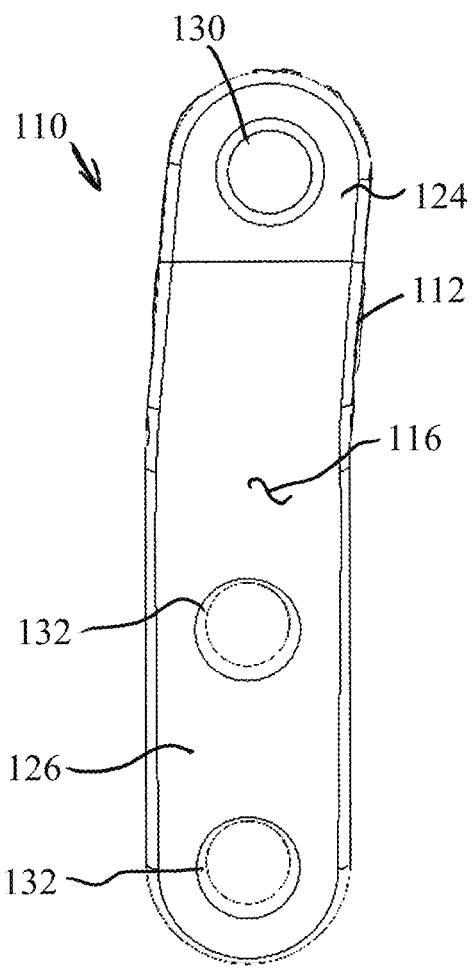
FIG. 17 is a top view of the fixation device of FIG. 11.
Figure 18:
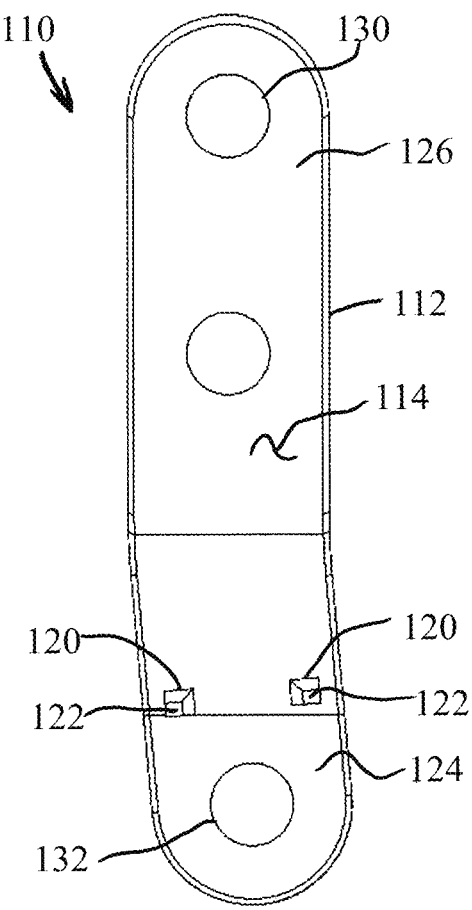
FIG. 18 is a bottom view of the fixation device of FIG. 11.
Figure 19:
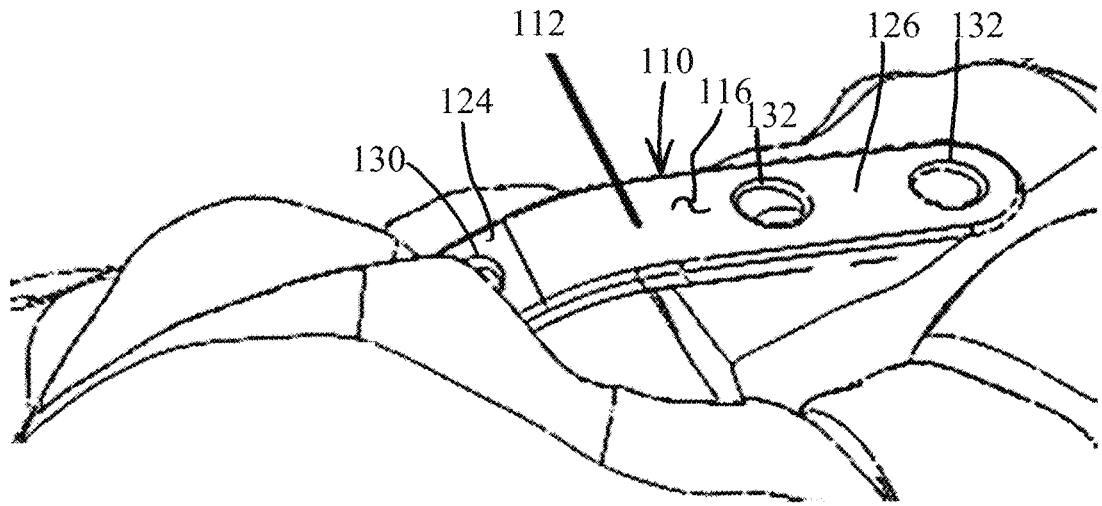
FIG. 19 is a an elevational perspective view of the fixation device of FIG. 11 implemented with bone segments of an exemplary the Calcaneal-Cuboid joint.
Figure 20:
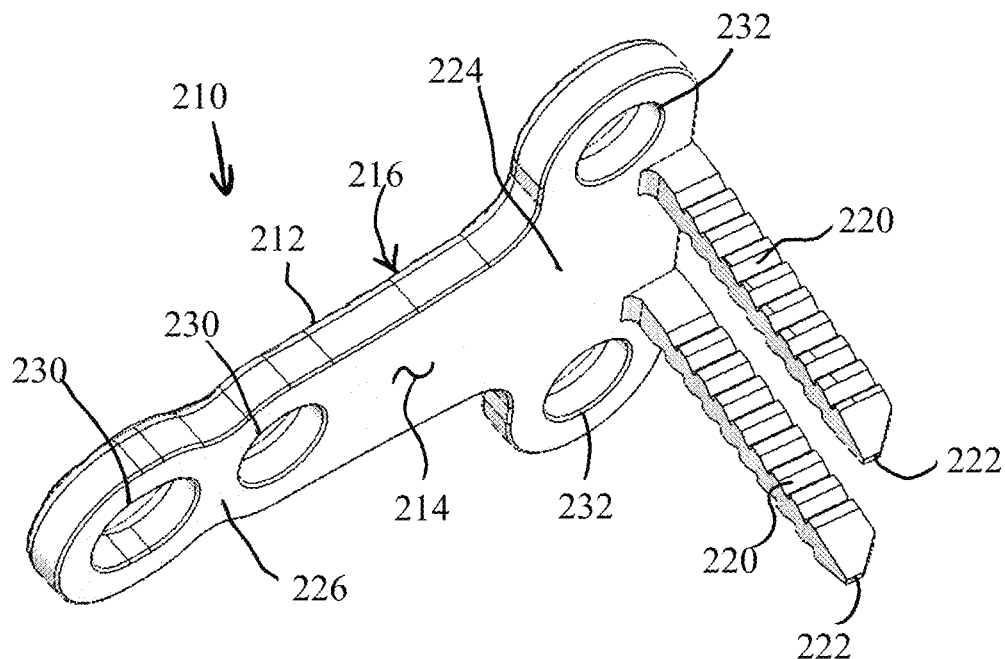
FIG. 20 is a bottom perspective view of the Talar-Navicular joint fixation device of FIG. 1 according to the present disclosure.
Figure 21:
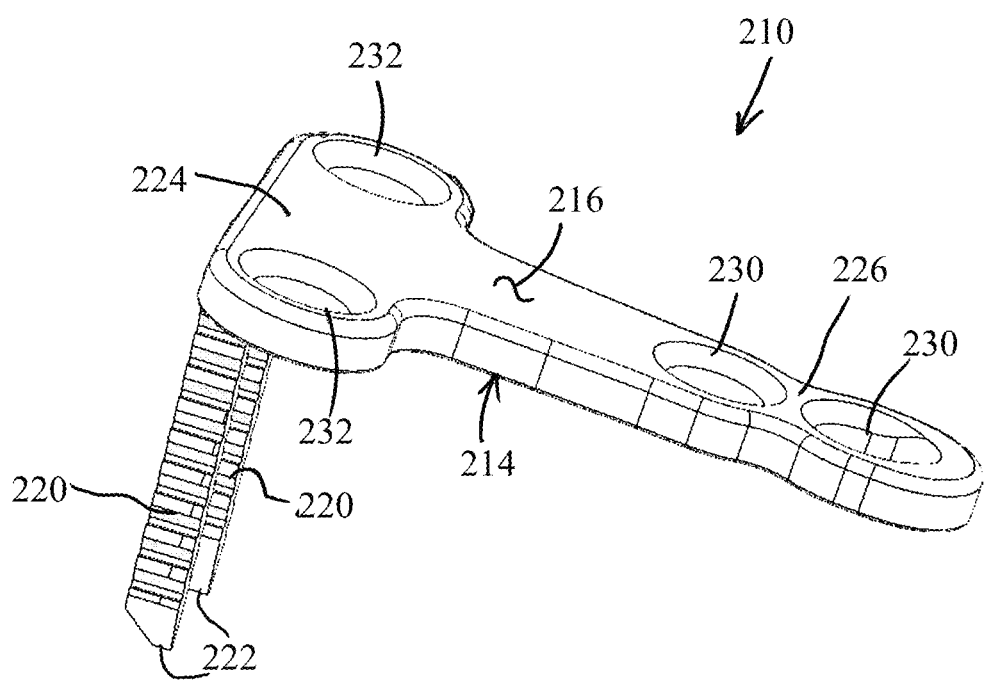
FIG. 21 is an elevational perspective view of the fixation device of FIG. 20.

Another example of a fixation device 110 that promotes or achieves bone fusion according to the present disclosure is shown in FIGS. 11-19. The device 110 is substantially similar to the device 10 of FIGS. 2-10 described above, and therefore the description of the aspects and features of device 10 above equally applies to device 110. The device 110 of FIGS. 11-19 may differ from the device 110 of FIGS. 2-10 in that the device 110 may be particularly well suited for fixation of the bone segments of the Calcaneal-Cuboid joint, as shown in FIGS. 1 and 19. As shown in FIGS. 1 and 19, the proximal portion 124 of the plate portion 112 of the device 110 may be affixed to a calcaneus bone (i.e., the second bone segment) and the distal portion 126 of the of the plate portion 112 may be affixed a corresponding cuboid bone (i.e., the first bone segment).

Figure 13:
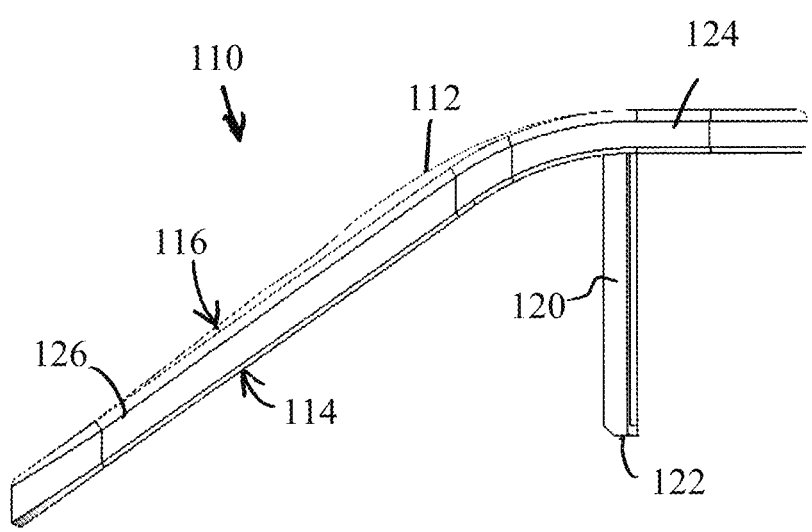
FIG. 13 is a left side view of the fixation device of FIG. 11.
Figure 14:
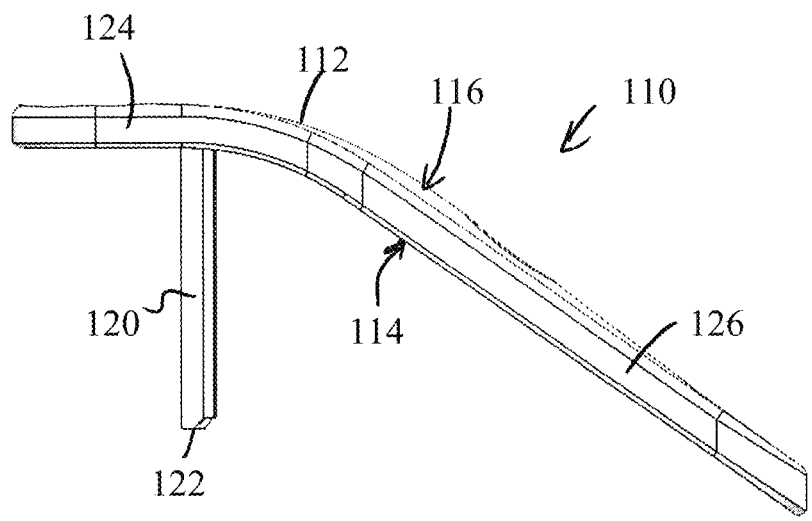
FIG. 14 is a right side view of the fixation device of FIG. 11.
Figure 15:
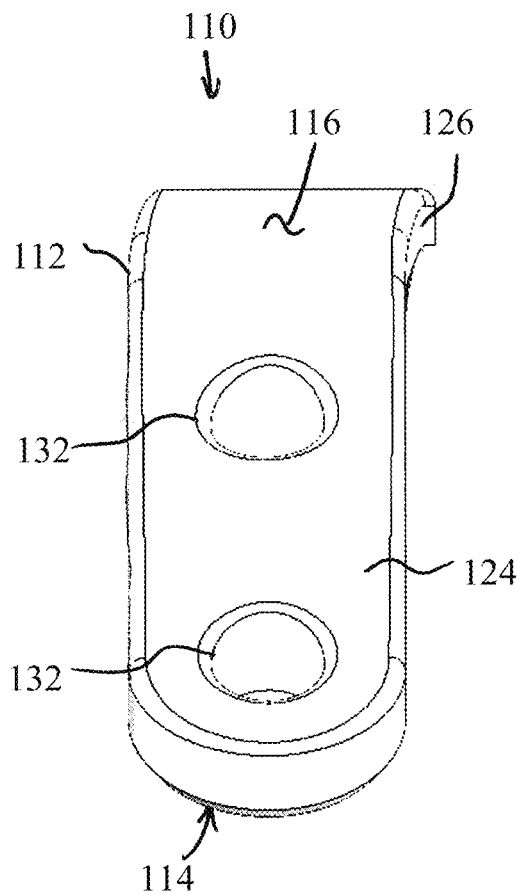
FIG. 15 is a back view of the fixation device of FIG. 11.
Figure 16:
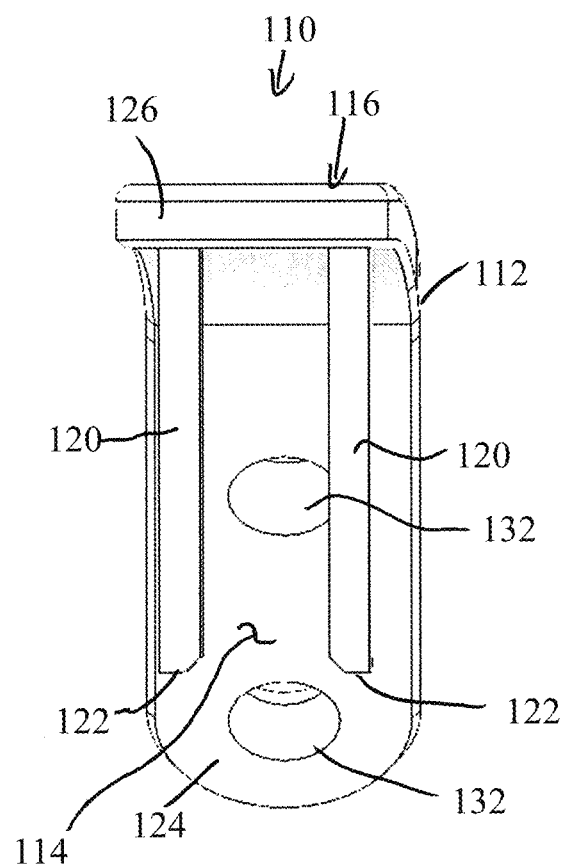
FIG. 16 is a front view of the fixation device of FIG. 11.

The relative orientation of the proximal and distal portions 124, 126 of the device 110 in the dorsal-plantar direction may be configured for fixation of the Calcaneal-Cuboid joint (and to promote fusion thereof). As shown in FIGS. 17 and 18, the proximal and distal portions 124, 126 of the plate portion 112 of the device 110 may be offset or angled with respect to each other in the dorsal-plantar direction to a greater extent than that of the device 10 of FIGS. 2-10. For example, the proximal and distal portions 124, 126 of the plate portion 112 may be offset or angled with respect to each other within about 0 degrees to about 45 degrees in the dorsal-plantar direction. As shown in FIGS. 13 and 14, the distal portion 126 of the plate portion 112 may extend further in the plantar-dorsal direction than the at least one bone engagement projection 120 when the proximal portion 124 is oriented substantially horizontally.

As shown in FIGS. 18 and 19, the proximal and distal portions 124, 216 of the plate portion 112 may be offset or angled in the medial-lateral direction to a lesser extent as compared to the device 10 of FIGS. 2-10. Similarly, the at least a pair of bone engagement projections 120, 120 may be oriented on an angle with respect to the distal portion 126 to a lesser extent as compared to the device 10. In some embodiments, the proximal and distal portions 124, 126 of the device 110 (and, potentially, the arrangement of the at least one bone engagement projection 120) may be offset or angled with respect to each other within about 0 degrees to about 35 degrees in the medial-lateral direction. Further, the intersection of the proximal and distal portions 124, 126 of the plate portion 112 may be a sharper transition than that of device 10, such as being defined by a smaller radius.

The proximal portion 124 of the plate portion 112 may include a pair of substantially circular fixation apertures 132, as shown in FIGS. 11, 12 and 15-19. However, as shown in FIGS. 11, 12 and 15-19, the proximal portion 124 of the plate portion 112 may not include a compression slot.

Figure 26:
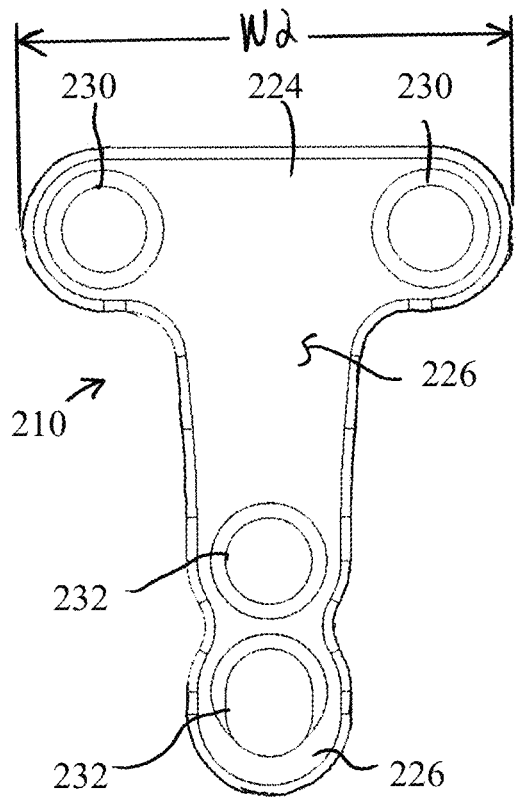
FIG. 26 is a top view of the fixation device of FIG. 20.
Figure 27:
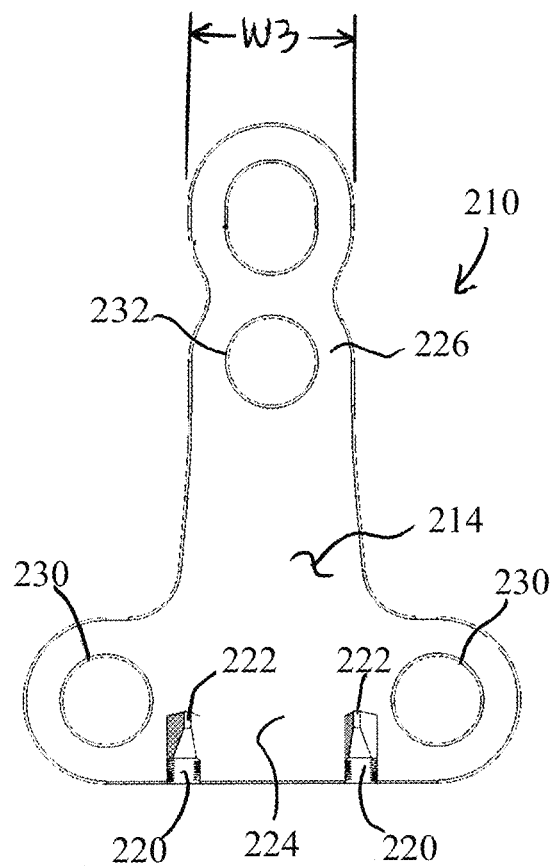
FIG. 27 is a bottom view of the fixation device of FIG. 20.
Figure 28:
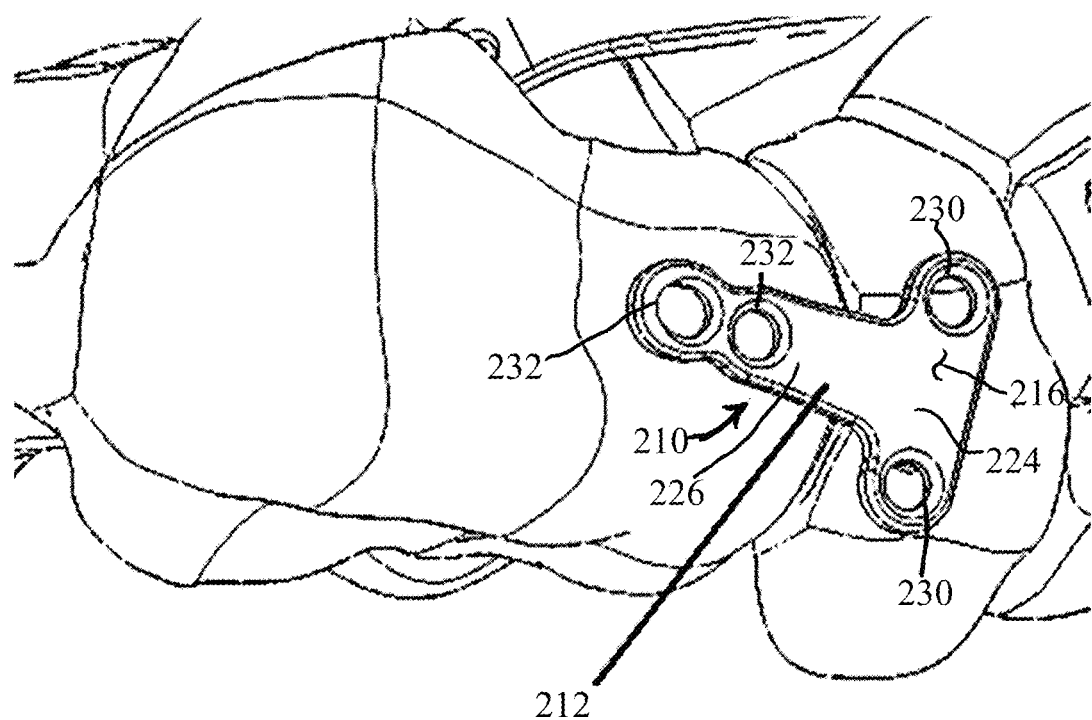
FIG. 28 is an elevational perspective view of the fixation device of FIG. 20 implemented with bone segments of an exemplary the Talar-Navicular joint.
Figure 29:
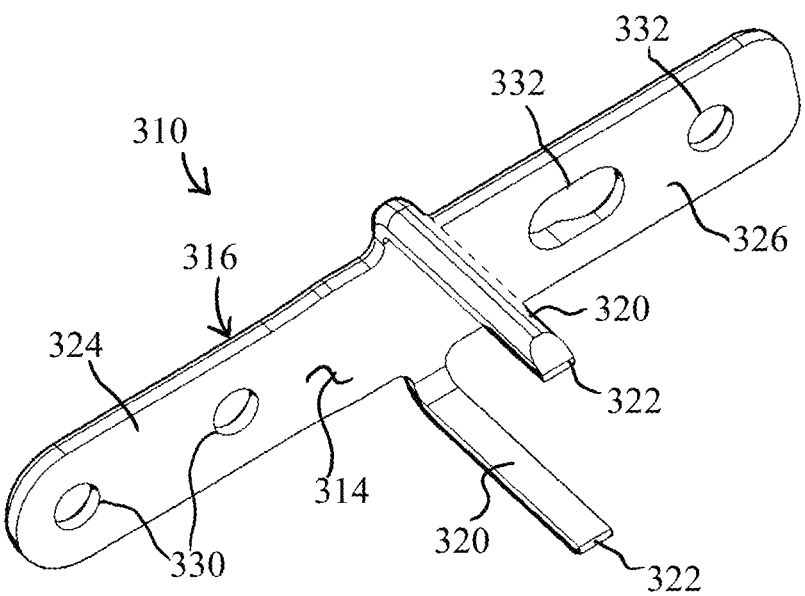
FIG. 29 is a bottom perspective view of a universal bone segment fixation device according to the present disclosure.
Figure 30:
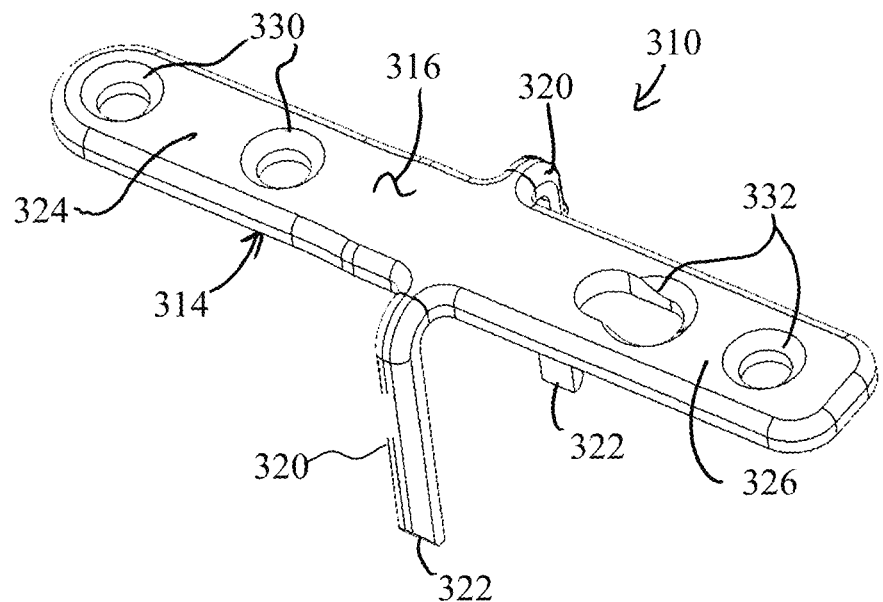
FIG. 30 is an elevational perspective view of the fixation device of FIG. 29.
Figure 31:
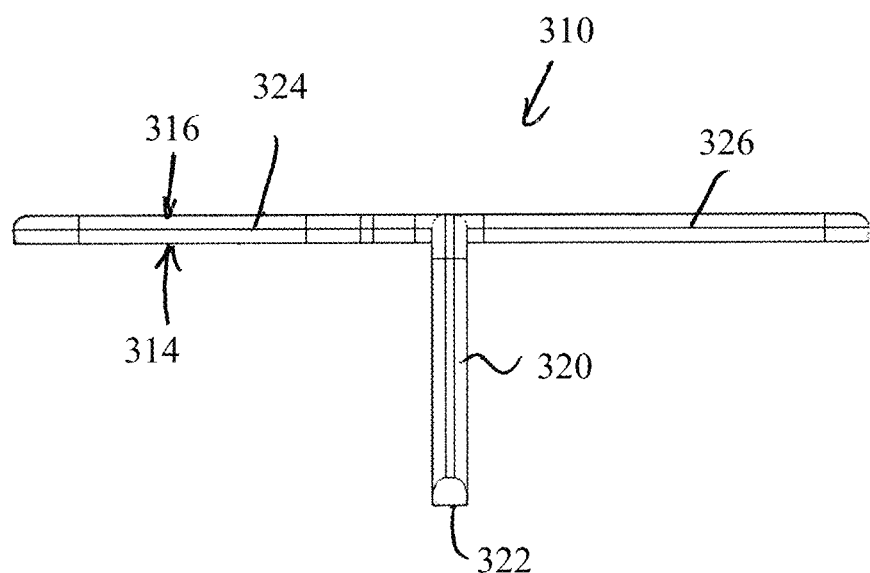
FIG. 31 is a left side view of the fixation device of FIG. 29.

Another example of a fixation device 210 according to the present disclosure is shown in FIGS. 20-28. The device 210 is substantially similar to the device 10 of FIGS. 2-10 and the device 110 of FIGS. 11-19 described above, and the description herein directed to devices 10 and 100 equally applies to the device 210 of FIGS. 20-28. The device 210 may differ from the devices 10 and 110 described above in that the device 210 may particularly well suited for fixation of the bone segments of the Talo-Navicular joint, as shown in FIG. 1 and FIG. 28.

As shown in FIG. 1 and FIG. 28, the proximal portion 224 of the plate portion 212 of the device 210 may be affixed to a navicular bone (i.e., the second bone segment) and the distal portion 226 of the device 210 may be affixed to a corresponding talus bone (i.e., the first bone segment). The shape and/or relative orientation of the proximal and distal portions 224, 226 of the device 210 may be configured for fixation of the Talo-Navicular joint (and to promote fusion thereof).

Figure 24:
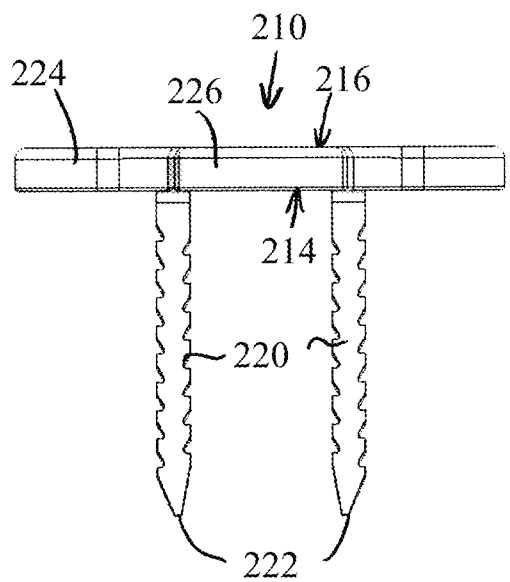
FIG. 24 is a back view of the fixation device of FIG. 20.
Figure 25:
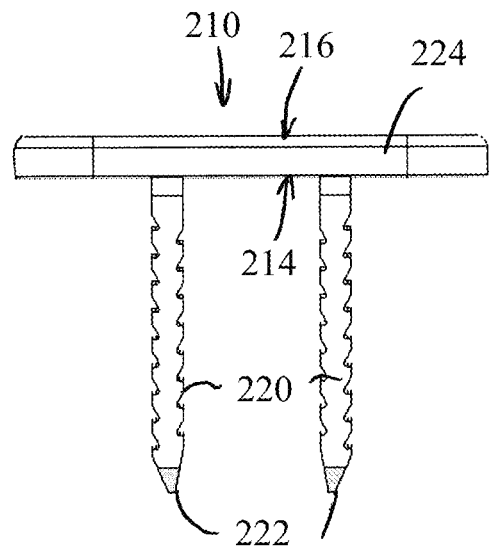
FIG. 25 is a front view of the fixation device of FIG. 20.

As shown in FIGS. 26 and 27, a medial-lateral width W2 of the proximal portion 224 of the device 210 may be substantially greater than the medial-lateral width W3 of the distal portion 226. When viewed along the plantar-dorsal direction, as shown in FIGS. 26 and 27, the device 210 is substantially T-shaped. The outer portions of the proximal portion 224 in the medial-lateral direction each include a substantially circular fixation aperture 230, 230 and at least one bone engagement projection 220 extending from the engagement surface 214 of the plate portion 212 positioned between the fixation apertures 230, 230 in medial-lateral direction. In some embodiments, as shown in FIGS. 20-25 and 27, the proximal portion 224 may include a pair of bone engagement projections 220, 220 extending from the engagement surface 214 and positioned between the fixation apertures 230, 230 in medial-lateral direction.

As also shown in FIGS. 26 and 27, the distal portion 226 may taper in the medial-lateral direction as is extends in the proximal-distal direction away from the proximal portion 224. As shown in FIGS. 20, 21 and 26-28, the distal portion 226 may include at least one substantially circular fixation aperture 232 and at least one compression slot 232, with a compression slot 232 positioned further in the proximal-distal direction away from the proximal portion 224 than a circular fixation aperture 232. The compression slot 232 may be positioned proximate to the end or tip of the distal portion 226 in the proximal-distal direction. As also shown in FIGS. 20, 21 and 26-28, the distal portion 226 may include a neck or narrow region in the medial-lateral direction between the substantially circular fixation aperture 232 and compression slot 232 in the proximal-distal direction.

Figure 22:
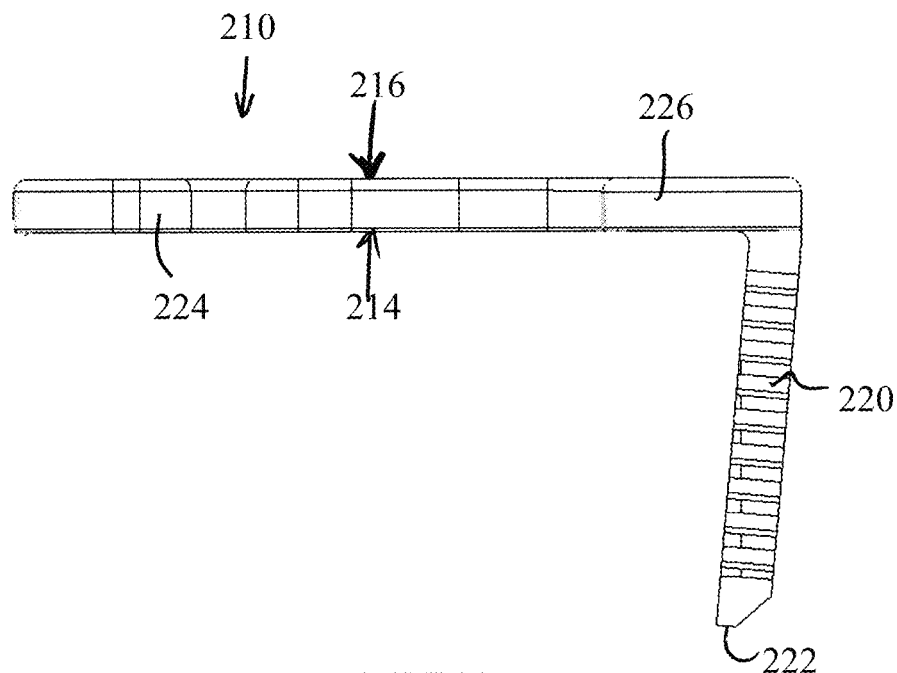
FIG. 22 is a left side view of the fixation device of FIG. 20.
Figure 23:
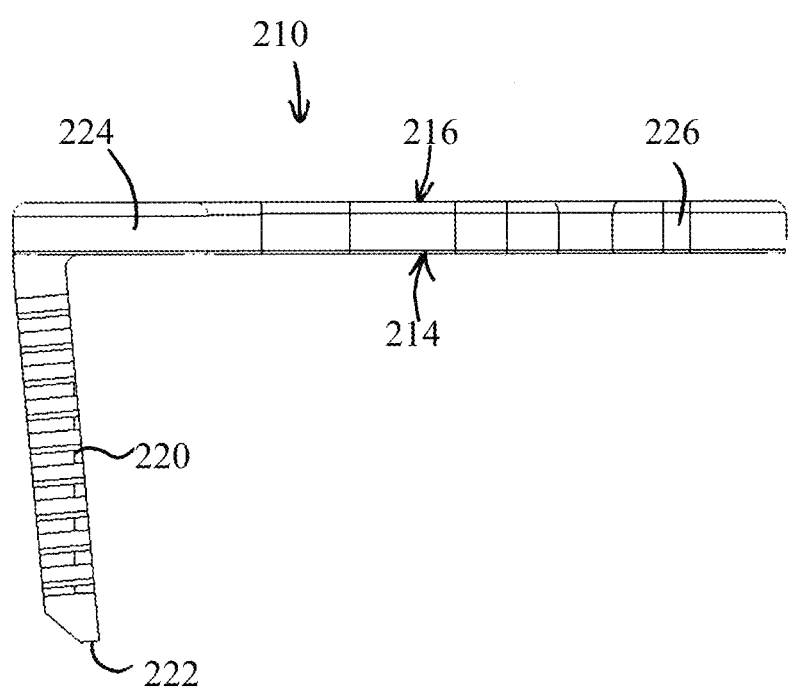
FIG. 23 is a right side view of the fixation device of FIG. 20.

The device 210 may be substantially flat or planar in the dorsal-plantar direction, as shown in FIGS. 22-25. Stated differently, the proximal and distal portions 224, 226 of the plate portion 212 may be aligned in the dorsal-plantar direction. However, as shown in FIGS. 22 and 23 the at least one bone engagement projection 220 may be angled relative to engagement surface 216 of the plate portion 212 (i.e., relative to the proximal and distal portions 224, 226). For example, the at least one bone engagement projection 220 may be angled toward the distal portion 226 as they extend away from the engagement surface 216. In some embodiments, the at least one bone engagement projection 220 may be angled at an obtuse angle with respect to the engagement surface 216 of the proximal portion 224. In some embodiments, the at least one bone engagement projection 220 may be angled within the range of about 80 degrees and about 90 degrees with respect to the engagement surface 216 of the proximal portion 224.

The at least one bone engagement projection 220 extending from the engagement surface 216 of the proximal portion 224 may be positioned at the edge of the proximal portion 224 in the proximal-distal direction. If the device 210 includes a pair of bone engagement projections 220, 220, as shown in FIG. 27, both the projections 220, 220 may extend from the engagement surface 216 of the proximal proximate to the edge of the proximal portion 224 in the proximal-distal direction, and each projection 220 may be positioned proximate to a corresponding fixation aperture 230. The at least one bone engagement projection 220 may include recesses or projections along their length to facilitate bone engagement, as shown in FIGS. 24 and 25.

Another example of a fixation device 310 according to the present disclosure is shown below in FIGS. 29-36. The device 310 is substantially similar to the devices 10, 110 and 210 described above, and therefore the description of devices 10, 110 and 210 applies equally to the device 310. The device 310 differs from the above-described devices 10, 110 and 210 in that it is particularly well suited for universal use in a variety of differing first and second bone segments (e.g., first and second small bone segments). The device 310 may be contoured or shaped (e.g. bent, twisted, angled, etc.) into a final configuration for use with particular first and second bone segments. In this way, the final shape or configuration of the device 310 may be dependent upon or related to the shape or configuration of the particular first and second bone segments to be fixed.

Figure 35:
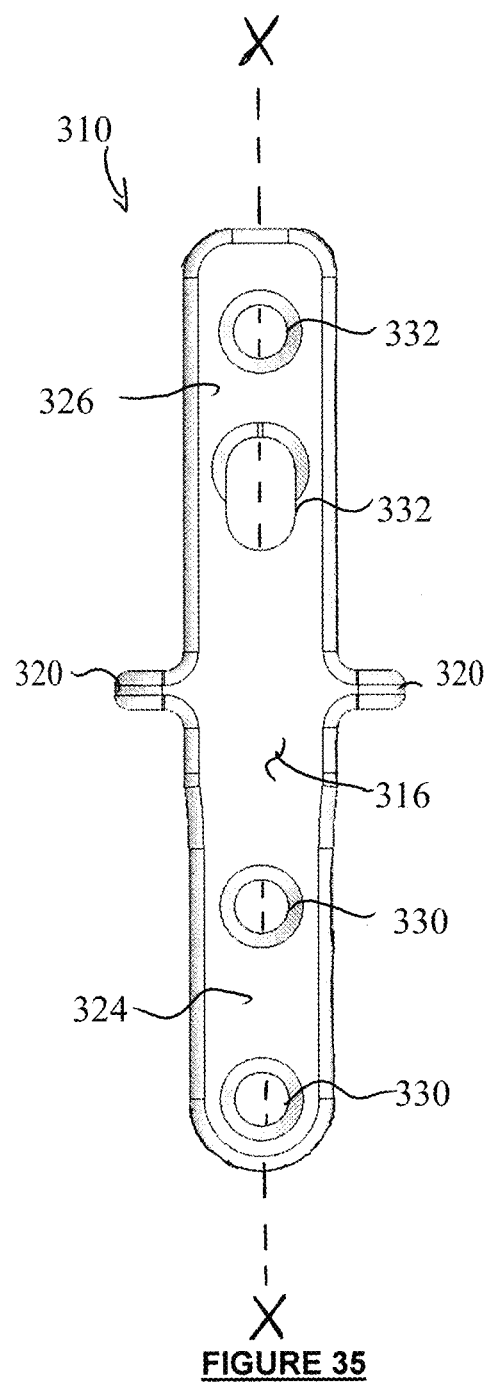
FIG. 35 is a top view of the fixation device of FIG. 29.
Figure 36:
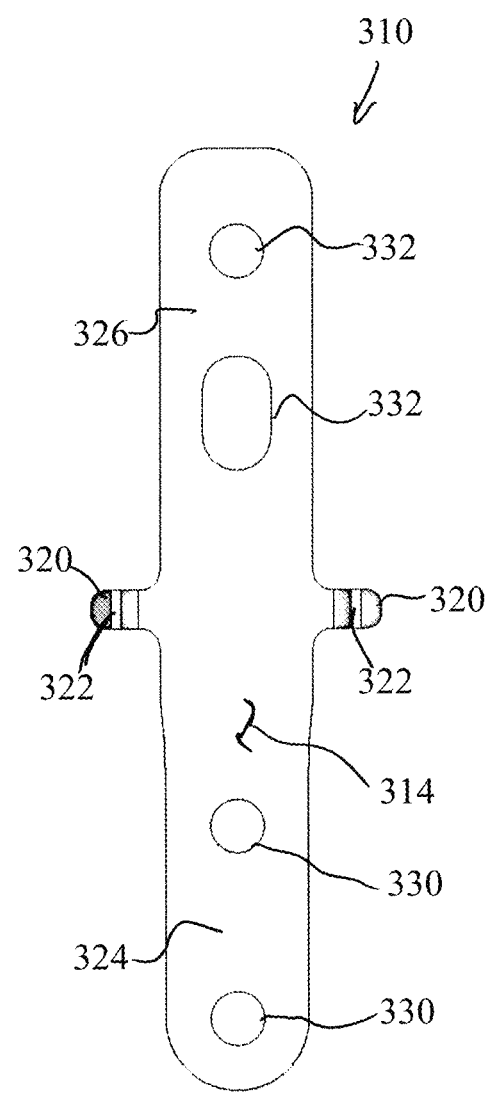
FIG. 36 is a bottom view of the fixation device of FIG. 29.

The proximal portion 324 of the device 310 may be slightly narrower in the medial-lateral direction than the proximal portion 324, as shown in FIGS. 35 and 36. For example, as shown in FIGS. 35 and 36 the proximal portion 324 may be narrow in the medial-lateral direction in an end region proximate the end of the proximal portion 324 in the proximal-distal direction than in a medial or intermediate portion of the plate portion 312 in the proximal-distal direction. As shown in FIGS. 35 and 36, the proximal portion 324 may include a relatively wider portion in the medial-lateral direction in a medial or intermediate portion of the plate portion 312 in the proximal-distal direction proximate to the at least one bone engagement projection 320. The relatively narrower portion of the proximal portion 324 of the plate portion 312 may include a pair of substantially circular fixation apertures 330 spaced in the proximal-distal direction, as shown in FIGS. 29, 30, 35 and 36.

The proximal and distal portions 334, 326 of the device 310 may extend substantially linearly along a central axis X-X of the device 310 that extends through the free ends of the device 310 in the proximal-distal direction, as shown in FIG. 35. As also shown in FIG. 35, the central axis X-X of the device 310 may extend through the middle of the center of the proximal and/or distal portions 334, 326 of the device 310 in the medial-lateral direction. For example, the proximal and distal portions 334, 326 of the device 310 may be substantially aligned in the dorsal-plantar and proximal-distal directions. The distal portion 326 may include a substantially circular fixation aperture 332 and a compression slot 332 spaced in the proximal-distal direction, with the substantially circular fixation aperture 332 positioned proximate to the distal side or edge of the device 310 in the proximal-distal direction, as shown in FIGS. 29, 30, 35 and 36. As noted above, the proximal portion 324 may include a pair of substantially circular fixation apertures 330 spaced in the proximal-distal direction, as shown in FIGS. 29, 30, 35 and 36. One of the apertures 330 may be positioned proximate to the distal side or edge of the device 310 in the proximal-distal direction.

As shown in FIGS. 29, 30, 35 and 36, the edge of the proximal portion 324 of the plate portion 312 of the device 310 in the proximal-distal direction may be substantially linear. As also shown in FIGS. 29, 30, 35 and 36, the edge of the distal portion 326 of the plate portion 312 of the device 310 in the proximal-distal direction may be substantially convex, such as being rounded.

The device 310 of FIGS. 29-36 also differs from the other devices 10, 110 and 210 described herein in that the at least one bone engagement projection 320 may extend out from a medial-lateral side of the plate portion 312 (in the medial-lateral direction), and/or be positioned in a medial or intermediate portion of the plate portion 312 in the proximal-distal direction. As shown in FIGS. 31, 32, 35 and 36, the device 310 may include at least a pair of bone engagement projection 320 that extend from opposing medial-lateral sides of the plate portion 312 at approximately the midpoint of the plate portion 312 in the proximal-distal direction. The illustrated bone engagement projections 320, 320 thereby do not extend from the engagement surface 314 of the proximal or distal portions 324, 326 of the plate proportion 312, but rather from the medial-lateral sides of the plate portion 312. As shown in FIGS. 30 and 33-36, the at least one bone engagement projection 320 may initially extend from a medial-lateral side of the plate portion 312 in the medial-lateral direction, and then curve or bend to extend in a substantially dorsal-to-planter direction. In alternative embodiments, at least a portion of the at least one bone engagement projection 320 may be angled in the medial-to-lateral direction, the lateral-to-medial direction, proximal-to-distal direction, distal-to-proximal direction or a combination thereof.

A surgical technique or method of utilizing the devices and systems described herein to fix (or promote fusion) of first and second bone segments may include exposure and cutting of the first and/or second bone segments. The cuts in the first and/or second bone segments may be based on a guide that is placed over the bones. In an alternative embodiment, the first and/or second bone segments may not be cut. The position of the first bone segment and the second bone segment may then be aligned or offset to a desired correction distance, offset, or angle. At least one hole may be formed into the second bone segment, and a plate portion of a device may be positioned over the first bone segment and the second bone segment such that the at least one bone engagement projection of the proximal portion of the plate portion of the device is positioned to engage the second bone segment hole(s). The at least one bone engagement projection(s) of the device may then be inserted into the second bone segment hole(s). In an alternative embodiment, the at least one bone engagement projection may be driven into the second bone segment without pre-drilling. At least one bone fixation mechanism may then be inserted into the second bone segment through at least one fixation aperture of the proximate portion of the plate portion fully secure the second bone segment to the device. At least one bone fixation mechanism may then be inserted into the first bone segment through at least one fixation aperture (e.g., a compression slot) of the distal portion of the plate portion to secure the first bone segment and the second bone segment and form a corrective construct.

The embodiments described herein may also be used to stabilize broken or fragmented bones having fragments that are difficult to capture. The embodiments described herein may also be used to fuse bone joints, typically after bone joint failure, when the bone joints have been stripped of articular cartilage.

Components or portions of the devices described herein may be distinct components or aspects that are coupled or attached to form the devices, or the devices may be monolithic (of one-piece construction). For example, the plate portions and the bone engagement projections may be separate and distinct structures that are coupled, or may be of one-piece construction.

A depiction and/or description of a substantially circular bone fixation aperture described with respect to a particular portion of a device or a particular device may equally apply to a substantially circular bone fixation depicted or described with respect to a differing portion of a device or a differing device. Similarly, depiction and/or description of a compression slot described with respect to a particular portion of a device or a particular device may equally apply to a compression slot depicted or described with respect to a differing portion of a device or a differing device.

While the embodiments described herein each embody different characteristics, it is understood to one of ordinary skill in the art that features of all embodiments described herein with respect to each of the individual Figures may be combined with features described with respect to other Figures of the present disclosure. Furthermore, any of the embodiments described herein are not meant to be limiting and any combination of features of the embodiments described herein that could or would be implemented by one of ordinary skill in the art should be recognized.

It is to be understood that the above description is intended to be illustrative, and not restrictive. Numerous changes and modifications may be made herein by one of ordinary skill in the art without departing from the general spirit and scope of the disclosure as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A fixation device for fixing bone segments, comprising:
a top surface and a bone engagement surface;
a proximal portion including a fixation aperture configured for acceptance of a bone fixation mechanism therethrough and into a first bone segment;
a distal portion including a second bone fixation aperture configured for acceptance of a bone fixation mechanism therethrough and into a second bone segment;
a pair of bone engagement projections connected to and extending from locations on the bone engagement surface for implantation into the first bone segment such that said pair of bone engagement projections extend normally from the locations relative to a longitudinal dimension of said proximal portion, said pair of bone engagement projections connected to said bone engagement surface at the locations spaced from lateral-most edges of said proximal portion in a medial-lateral direction and spaced from a proximal-most edge of said proximal portion in a proximal-distal direction; and
said distal portion being shaped in a longitudinal direction such that said distal portion extends dorsally further than said pair of bone engagement projections when said bone engagement surface engages the first bone segment and the second bone segment.

2. The fixation device of claim 1, wherein said distal portion extends dorsally further than said proximal portion when said proximal portion is orientated substantially horizontally.

3. The fixation device of claim 1, wherein the proximal and distal portions are angled with respect to each other in the medial-lateral direction.

4. The fixation device of claim 1, wherein the proximal and distal portions are angled with respect to each other in the plantar-dorsal direction.

5. The fixation device of claim 4, wherein the bone engagement projections extend from the bone engagement surface in the plantar-dorsal direction, and wherein the bone engagement projections extend further in the plantar-dorsal direction than the distal portion when the proximal portion is orientated substantially horizontally.

6. The fixation device of claim 4, wherein the bone engagement projections extend from the bone engagement surface in the plantar-dorsal direction a distance further than that of the distal portion when the proximal portion is orientated substantially horizontally.

7. The fixation device of claim 1, wherein the proximal and distal portions are elongated in the proximal-distal direction, and wherein the distal portion defines a total length in the proximal-distal direction greater than a total length of the proximal portion in the proximal-distal direction.

8. The fixation device of claim 1, wherein the proximal and distal portions each define a width in the medial-lateral direction, and wherein the width of the proximal portion is greater than the width of the distal portion.

9. The fixation device of claim 8, wherein the distal portion is elongated in the proximal-distal direction, and wherein the width of the distal portion tapers as it extends in the proximal-distal direction away from the proximal portion.

10. The fixation device of claim 9, wherein the distal portion includes a narrow region in the medial-lateral direction positioned at least partially between the first aperture and the second aperture in the proximal-distal direction.

11. The fixation device of claim 1, wherein the bone engagement projections extend from a proximal bone engagement surface of the bone engagement surface of the proximal portion.

12. The fixation device of claim 11, wherein the bone engagement projections extend normally from the engagement surface of the proximal portion.

13. The fixation device of claim 1, wherein the bone engagement projections extend from a medial-lateral side of the proximal portion.

14. The fixation device of claim 1, wherein the second aperture is a compression slot.

\* \* \* \* \*